(12) United States Patent
Keating et al.

(10) Patent No.: US 9,775,601 B2
(45) Date of Patent: Oct. 3, 2017

(54) LAPAROSCOPIC SURGICAL SYSTEM

(75) Inventors: Ronan Keating, Galway (IE); Gerard Rabbitte, Galway (IE); Barry Russell, Kildare (IE)

(73) Assignee: NEOSURGICAL LIMITED, Galway (IE)

( * ) Notice: Subject to any disclaimer, the term of this patent is extended or adjusted under 35 U.S.C. 154(b) by 690 days.

(21) Appl. No.: 13/641,014

(22) PCT Filed: Apr. 13, 2011

(86) PCT No.: PCT/EP2011/055862
§ 371 (c)(1),
(2), (4) Date: Dec. 18, 2012

(87) PCT Pub. No.: WO2011/128392
PCT Pub. Date: Oct. 20, 2011

(65) Prior Publication Data
US 2013/0103057 A1  Apr. 25, 2013

Related U.S. Application Data

(60) Provisional application No. 61/323,367, filed on Apr. 13, 2010.

(30) Foreign Application Priority Data

Dec. 17, 2010  (GB) .................................. 1021479.9

(51) Int. Cl.
*A61B 17/04*   (2006.01)
*A61B 17/34*   (2006.01)
(Continued)

(52) U.S. Cl.
CPC ...... *A61B 17/0469* (2013.01); *A61B 17/0401* (2013.01); *A61B 17/0482* (2013.01);
(Continued)

(58) Field of Classification Search
CPC ............ A61B 17/0482; A61B 17/3423; A61B 17/06061; A61B 1/32; A61B 17/0281;
(Continued)

(56) References Cited

U.S. PATENT DOCUMENTS 3,409,014 A * 11/1968 Shannon ....................... 606/148
5,330,437 A *  7/1994 Durman .................... 604/167.04
(Continued)

FOREIGN PATENT DOCUMENTS

| WO | 2004030515 A2 | 4/2004 |
| WO | 2005122911 A1 | 12/2005 |
| WO | 2011-128392 A1 | 10/2011 |

OTHER PUBLICATIONS

International Search Report and Written Opinion for PCT/EP2011/055862 dated Jun. 24, 2011; 14 pages.
(Continued)

*Primary Examiner* — Tuan V Nguyen
*Assistant Examiner* — Chima Igboko
(74) *Attorney, Agent, or Firm* — Schwabe Williamson & Wyatt, PC

(57) ABSTRACT

A laparoscopic port closure device is described. The device allows for the deployment of a suture internally into an abdominal wall and the subsequent use of that deployed suture to effect a closing of the wound that was used for the port. The deployed suture may be used during the surgical procedure to effect a securing or anchoring of the device.

16 Claims, 24 Drawing Sheets

(51) Int. Cl.
  *A61B 17/06* (2006.01)
  *A61B 17/00* (2006.01)

(52) U.S. Cl.
  CPC ...... *A61B 17/0491* (2013.01); *A61B 17/3421* (2013.01); *A61B 17/3423* (2013.01); *A61B 17/06061* (2013.01); *A61B 17/06128* (2013.01); *A61B 17/3496* (2013.01); *A61B 2017/00637* (2013.01); *A61B 2017/00663* (2013.01); *A61B 2017/0409* (2013.01); *A61B 2017/0414* (2013.01); *A61B 2017/0417* (2013.01); *A61B 2017/0437* (2013.01); *A61B 2017/0445* (2013.01); *A61B 2017/0464* (2013.01); *A61B 2017/06042* (2013.01); *A61B 2017/3441* (2013.01); *A61B 2017/3466* (2013.01)

(58) Field of Classification Search
  CPC ................ A61B 17/29; A61B 17/0469; A61B 17/06128; A61B 2017/00637; A61B 2017/0409; A61B 2017/0414; A61B 2017/3441; A61B 2017/3466
  USPC ....... 606/146, 144, 148, 129, 139, 147, 145, 606/113, 115, 185, 190, 213; 600/204
  See application file for complete search history.

(56) References Cited

U.S. PATENT DOCUMENTS

| | | | |
|---|---|---|---|
| 5,443,484 A * | 8/1995 | Kirsch et al. | 604/164.04 |
| 5,460,170 A * | 10/1995 | Hammerslag | 600/201 |
| 5,478,345 A | 12/1995 | Stone et al. | |
| 5,514,133 A * | 5/1996 | Golub et al. | 606/1 |
| 5,618,309 A | 4/1997 | Green et al. | |
| 5,634,937 A * | 6/1997 | Mollenauer et al. | 606/213 |
| 5,672,168 A * | 9/1997 | de la Torre et al. | 606/1 |
| 5,716,369 A | 2/1998 | Riza | |
| 5,827,299 A | 10/1998 | Thomason et al. | |
| 5,830,125 A * | 11/1998 | Scribner et al. | 606/139 |
| 5,891,159 A * | 4/1999 | Sherman et al. | 606/144 |
| 5,906,577 A * | 5/1999 | Beane et al. | 600/207 |
| 5,948,002 A | 9/1999 | Bonutti | |
| 5,954,732 A * | 9/1999 | Hart et al. | 606/144 |
| 6,059,800 A * | 5/2000 | Hart et al. | 606/144 |
| 6,143,004 A | 11/2000 | Davis et al. | |
| 6,168,598 B1 * | 1/2001 | Martello | 606/74 |
| 6,190,396 B1 | 2/2001 | Whitin et al. | |
| 6,203,554 B1 * | 3/2001 | Roberts | 606/144 |
| 6,383,208 B1 * | 5/2002 | Sancoff et al. | 606/213 |
| 6,440,063 B1 * | 8/2002 | Beane et al. | 600/207 |
| 6,478,028 B1 * | 11/2002 | Paolitto et al. | 128/898 |
| 6,488,692 B1 * | 12/2002 | Spence et al. | 606/153 |
| 6,589,167 B1 | 7/2003 | Shimomura et al. | 600/208 |
| 6,610,071 B1 * | 8/2003 | Cohn et al. | 606/148 |
| 6,770,084 B1 * | 8/2004 | Bain et al. | 606/144 |
| 7,344,495 B2 * | 3/2008 | Ravikumar et al. | 600/219 |
| 7,393,322 B2 * | 7/2008 | Wenchell | 600/208 |
| 7,850,600 B1 | 12/2010 | Piskun | 600/114 |
| 7,909,804 B2 * | 3/2011 | Stats | 604/288.01 |
| 7,951,117 B2 * | 5/2011 | Wingardner et al. | 604/164.09 |
| 7,967,748 B2 * | 6/2011 | Kistler et al. | 600/204 |
| 8,657,740 B2 * | 2/2014 | Bonadio et al. | 600/201 |
| 8,727,974 B2 * | 5/2014 | Kasvikis | 600/208 |
| 8,734,336 B2 * | 5/2014 | Bonadio et al. | 600/208 |
| 8,795,161 B2 * | 8/2014 | Carter | 600/184 |
| 8,961,406 B2 * | 2/2015 | Ortiz et al. | 600/204 |
| 9,395,339 B2 | 7/2016 | Sarr | |
| 2002/0111638 A1 * | 8/2002 | Whitin et al. | 606/144 |
| 2003/0010346 A1 * | 1/2003 | Paolitto et al. | 128/898 |
| 2003/0153921 A1 * | 8/2003 | Stewart et al. | 606/72 |
| 2003/0158562 A1 * | 8/2003 | Feigl | 606/148 |
| 2004/0015185 A1 * | 1/2004 | Ewers | A61B 17/0293 606/213 |
| 2004/0087833 A1 * | 5/2004 | Bauer et al. | 600/201 |
| 2004/0092965 A1 * | 5/2004 | Parihar | 606/144 |
| 2004/0138683 A1 | 7/2004 | Shelton | |
| 2004/0167543 A1 * | 8/2004 | Mazzocchi et al. | 606/130 |
| 2004/0167546 A1 | 8/2004 | Saadat et al. | |
| 2004/0176786 A1 | 9/2004 | Edoga et al. | |
| 2004/0254593 A1 * | 12/2004 | Fallin et al. | 606/148 |
| 2005/0065535 A1 | 3/2005 | Morris et al. | |
| 2005/0215863 A1 * | 9/2005 | Ravikumar et al. | 600/204 |
| 2005/0222582 A1 * | 10/2005 | Wenchell | 606/108 |
| 2005/0251206 A1 | 11/2005 | Maahs et al. | |
| 2005/0283192 A1 | 12/2005 | Torrie | |
| 2005/0288690 A1 | 12/2005 | Bourque et al. | |
| 2006/0178702 A1 | 8/2006 | Pierce | |
| 2006/0217762 A1 | 9/2006 | Maahs et al. | |
| 2006/0247500 A1 * | 11/2006 | Voegele | A61B 1/32 600/208 |
| 2007/0021781 A1 * | 1/2007 | Jervis et al. | 606/232 |
| 2007/0032823 A1 | 2/2007 | Tegg | |
| 2007/0049929 A1 | 3/2007 | Catanese et al. | |
| 2007/0112425 A1 | 5/2007 | Schaller et al. | |
| 2007/0225719 A1 | 9/2007 | Stone et al. | |
| 2008/0058584 A1 | 3/2008 | Hirotsuka et al. | |
| 2008/0097485 A1 | 4/2008 | Shpaichler et al. | |
| 2008/0140092 A1 | 6/2008 | Stone et al. | |
| 2008/0140093 A1 | 6/2008 | Stone et al. | |
| 2008/0208131 A1 * | 8/2008 | Powers et al. | 604/164.11 |
| 2008/0243148 A1 * | 10/2008 | Mikkaichi et al. | 606/144 |
| 2008/0255519 A1 * | 10/2008 | Piskun et al. | 604/174 |
| 2008/0294001 A1 * | 11/2008 | Surti | 600/104 |
| 2009/0036745 A1 * | 2/2009 | Bonadio et al. | 600/208 |
| 2009/0069823 A1 | 3/2009 | Foerster et al. | |
| 2009/0093683 A1 * | 4/2009 | Richard et al. | 600/204 |
| 2009/0157105 A1 | 6/2009 | Zung et al. | |
| 2009/0221966 A1 * | 9/2009 | Richard | 604/164.04 |
| 2009/0227843 A1 * | 9/2009 | Smith et al. | 600/208 |
| 2009/0287308 A1 | 11/2009 | Davis et al. | |
| 2009/0292176 A1 * | 11/2009 | Bonadio et al. | 600/203 |
| 2009/0326564 A1 | 12/2009 | White et al. | |
| 2010/0004665 A1 | 1/2010 | Hong et al. | |
| 2010/0010512 A1 | 1/2010 | Taylor et al. | |
| 2010/0023026 A1 | 1/2010 | Zeiner et al. | |
| 2010/0030262 A1 | 2/2010 | McLean et al. | |
| 2010/0063364 A1 * | 3/2010 | Bonadio et al. | 600/208 |
| 2010/0063452 A1 | 3/2010 | Edelman et al. | |
| 2010/0069930 A1 | 3/2010 | Roslin et al. | |
| 2010/0076462 A1 | 3/2010 | Bakos et al. | |
| 2010/0081880 A1 * | 4/2010 | Widenhouse et al. | 600/201 |
| 2010/0130824 A1 * | 5/2010 | Piskun | 600/204 |
| 2010/0222643 A1 | 9/2010 | Piskun et al. | |
| 2010/0262166 A1 | 10/2010 | Boraiah et al. | |
| 2010/0268035 A1 * | 10/2010 | Oberlander et al. | 600/204 |
| 2010/0312063 A1 * | 12/2010 | Hess et al. | 600/204 |
| 2011/0270194 A1 * | 11/2011 | Piskun | 604/165.01 |
| 2013/0090670 A1 | 4/2013 | Keating | |
| 2015/0053015 A1 | 2/2015 | Sarr | |
| 2015/0335320 A1 | 11/2015 | Keating | |

OTHER PUBLICATIONS

International Preliminary Report on Patentability for PCT/EP2011/055862 dated Oct. 16, 2012; 9 pages.

* cited by examiner

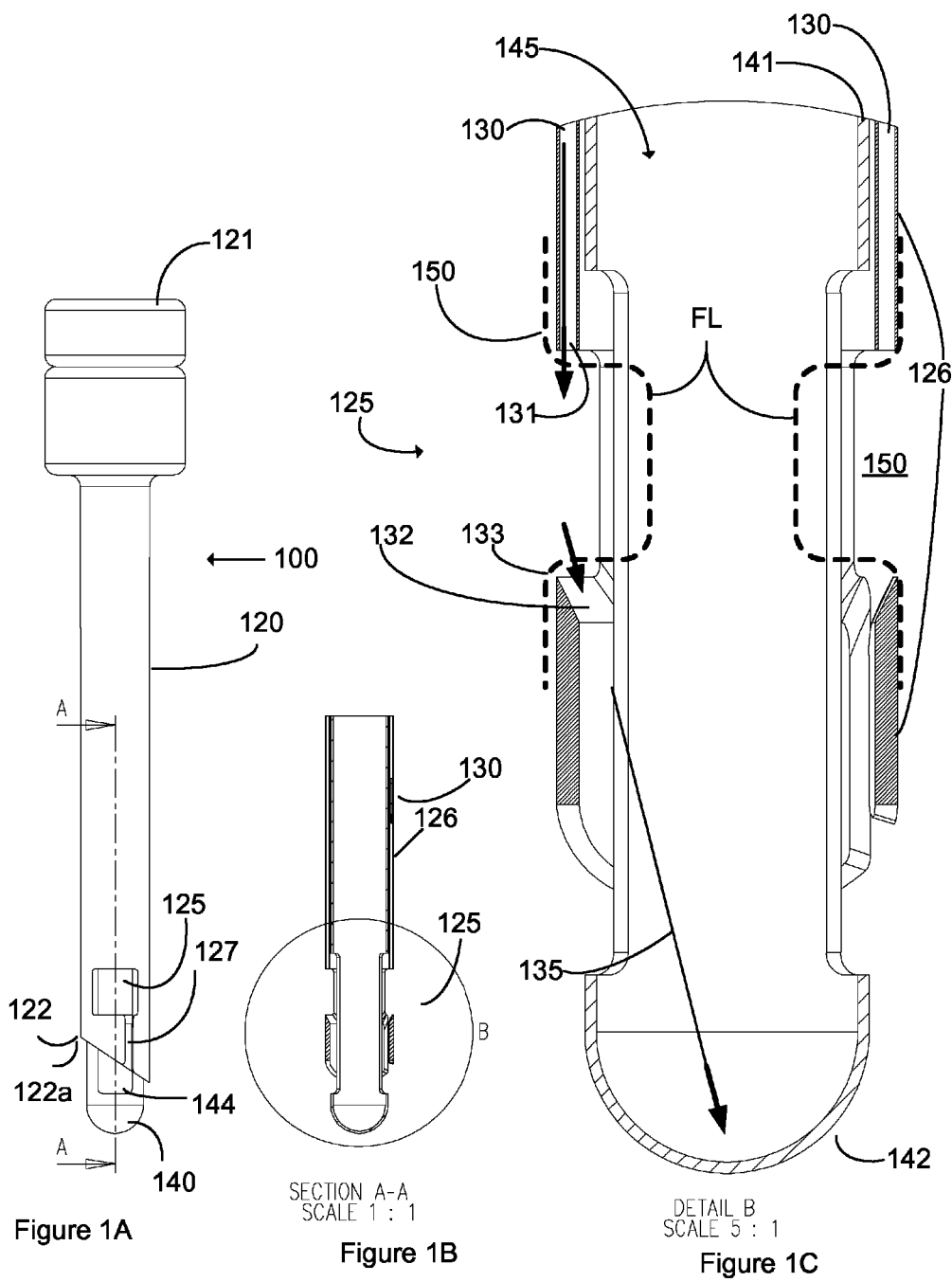

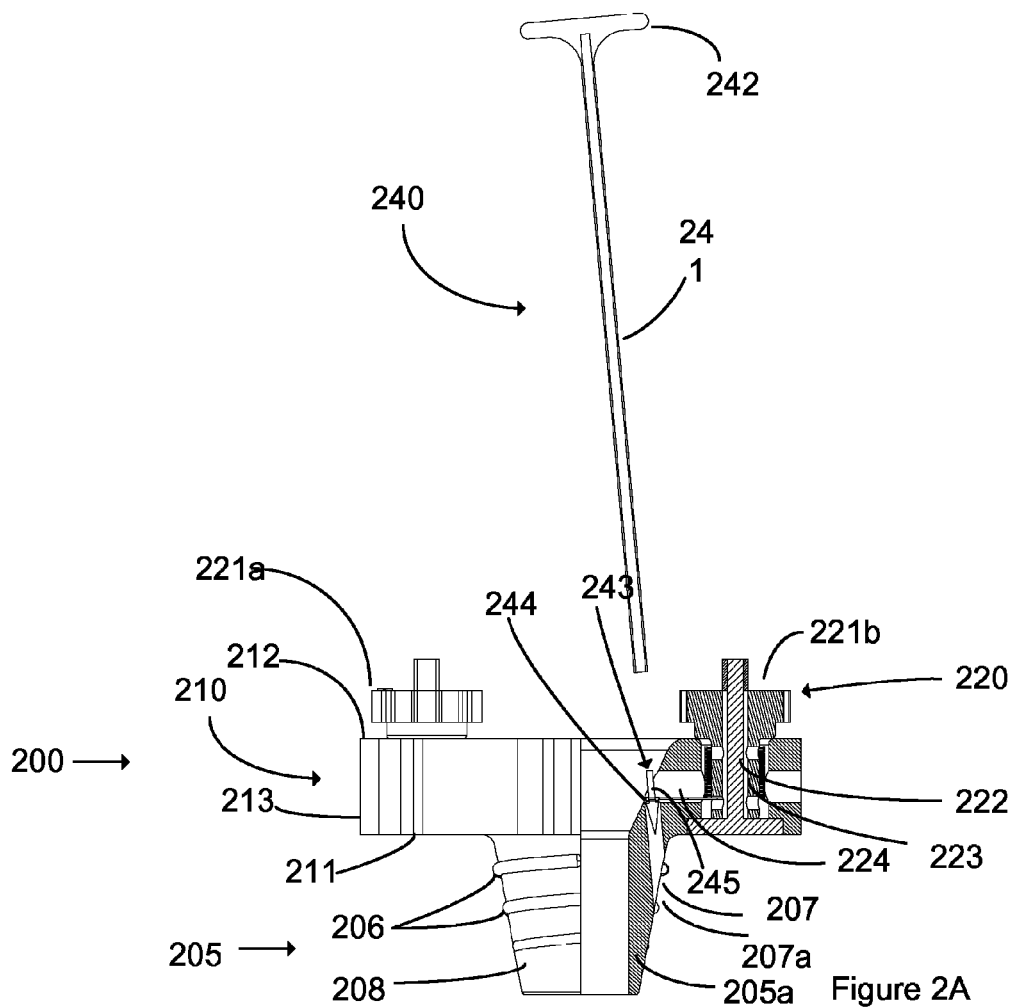
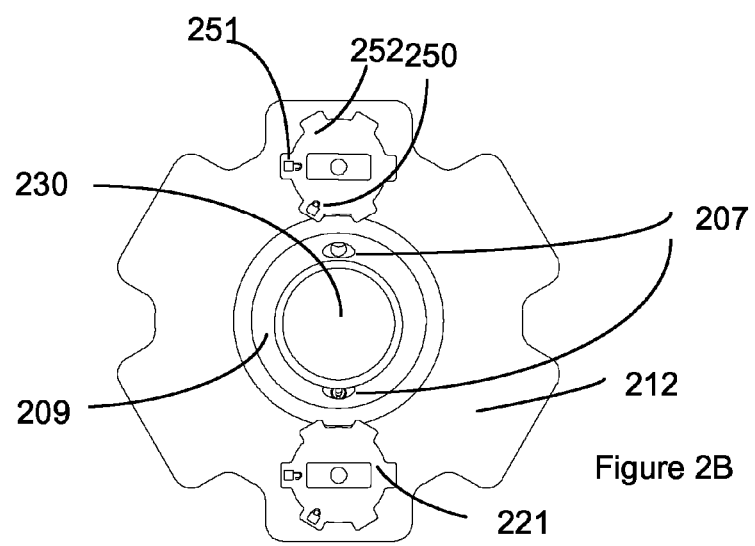

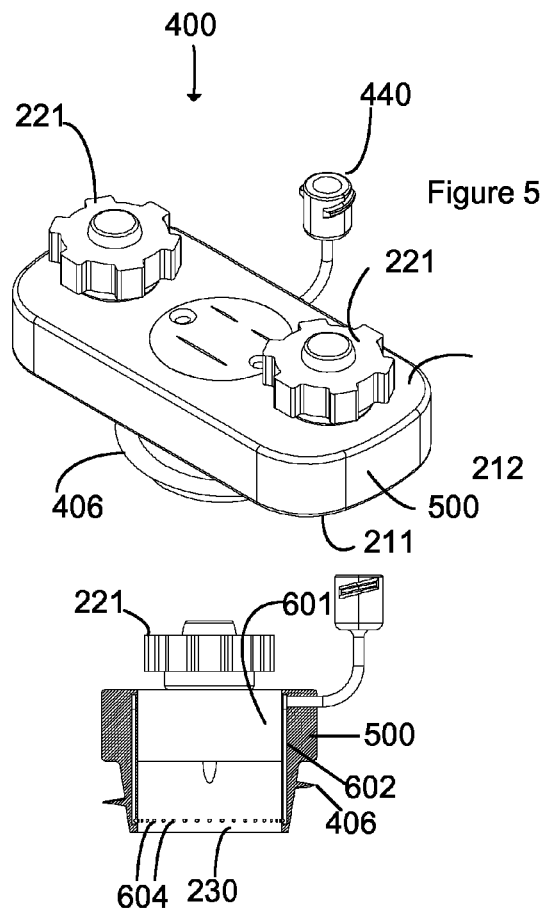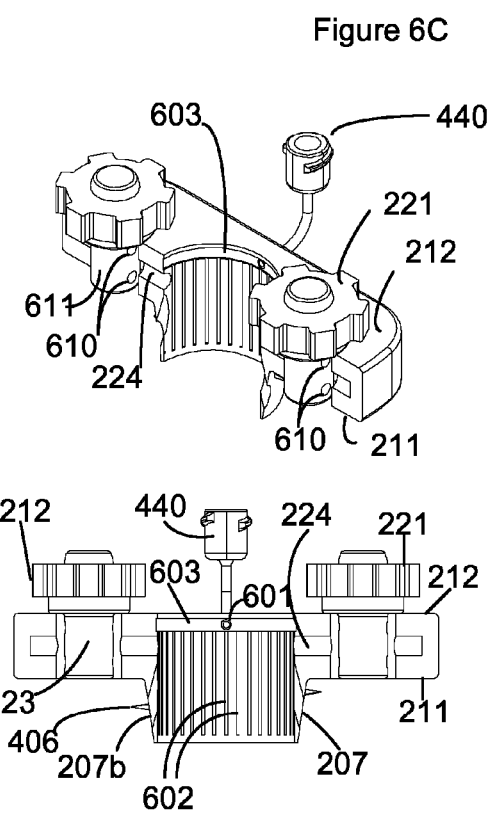

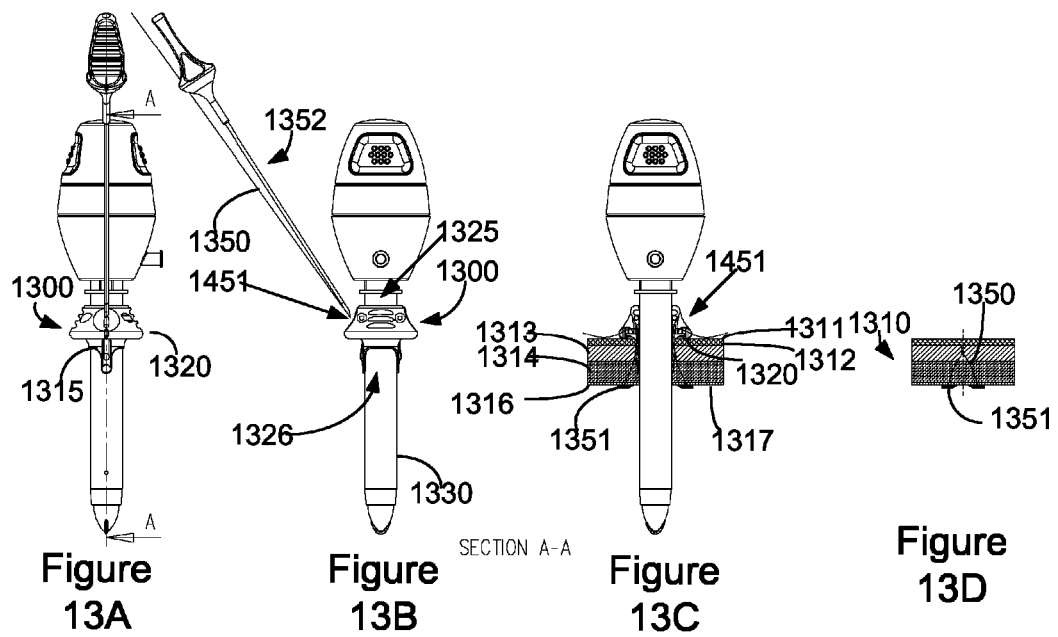

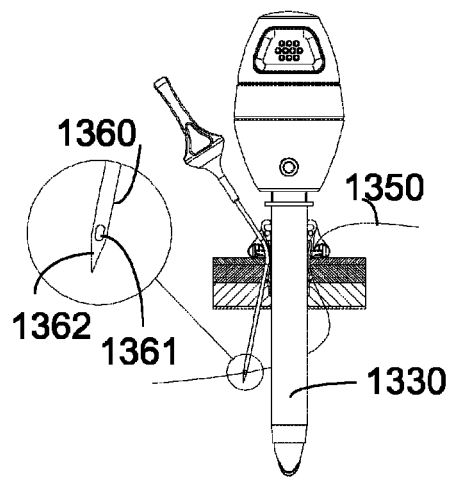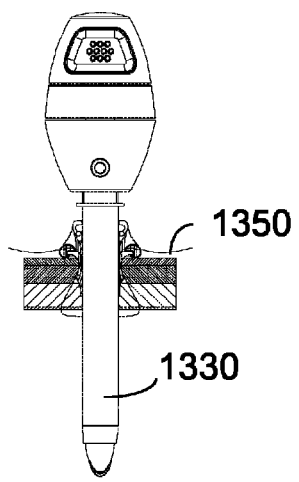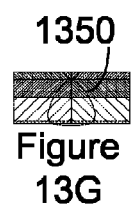
Figure 13E     Figure 13F

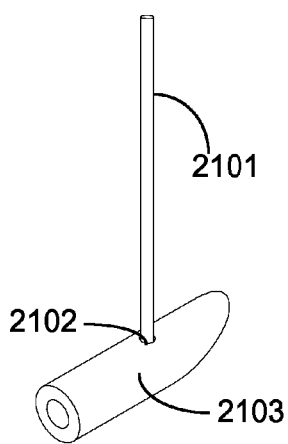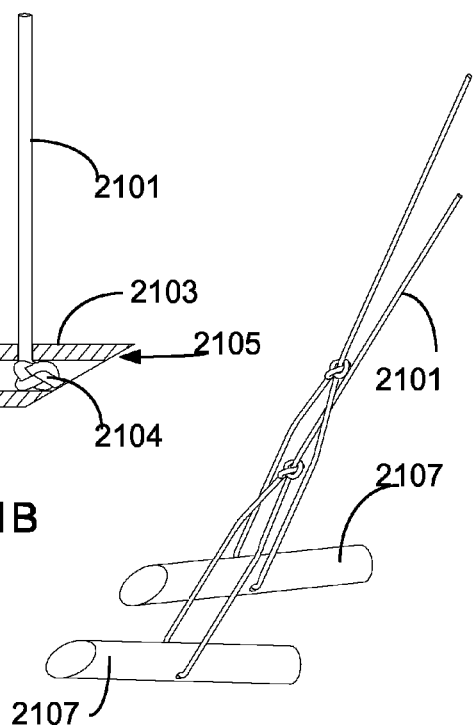
Figure 21A  Figure 21B  Figure 21C

LAPAROSCOPIC SURGICAL SYSTEM

FIELD OF THE INVENTION

The present invention relates to a laparoscopic surgical system. In one configuration it relates to an anchoring system which is usefully employed in laparoscopic surgery. In another configuration it relates to a closure system which is usefully employed in laparoscopic surgical procedures. The system may comprise a trocar and provide an anchoring and closure system for use in laparoscopic surgery.

BACKGROUND

There are difficulties sometimes associated with the closure of the trocar wound site for example, in laparoscopic procedures. There are difficulties in particular in finding the fascia layer through which a suture must be passed to ensure good and adequate port site closure.

With deeper port sites, such as with an obese patient, it is often more difficult for the surgeon to gain deep access to the fascial layer to securely place a suture therein. In certain instances it may be necessary to cut open the wound to accurately place a suture fixation on the inner fascia layer.

The consequences of inadequate closure may be serious. For example, the patient may be subject to an early or late onset hernia, bowel stricture and/or bleeding from the port site. All of these complications have varying associated morbidities up to and including fatalities in serious undetected bowel strictures. The rate of port site herniation is widely published to be up to 3% for the normal population and double this for the obese cohort.

There are therefore a number of problems with current methods of trocar port site closure that need to be addressed, particularly for the obese patient.

There are further difficulties in anchoring or otherwise securing laparoscopic surgical devices relative to a laparoscopic surgical port, in particular with Hasson type ports. Suture stays can be difficult to manage during Hasson trocar olive fixation and can become tangled when removing or adjusting the trocar. These problems also need to be addressed in order to ensure an efficient workflow for the surgeon.

SUMMARY

These needs and others are addressed by a laparoscopic device in accordance with the present teaching which provides for deployment of a suture and anchor to enable port site closure subsequent to a laparoscopic surgical procedure. In a preferred configuration the deployed suture is used to anchor the device during the laparoscopic procedure.

These and other features of the present teaching will be better understood with reference to the drawings which follow which are provided to assist in an understanding of the present teaching and are not to be construed as limiting in any fashion.

BRIEF DESCRIPTION OF THE DRAWINGS

The present teaching will now be described with reference to the accompanying drawings in which:

FIG. 1 shows a trocar and associated obturator that may be used in accordance with the present teaching to provide for a closure of a laparoscopic port with FIG. 1A showing a side view, FIG. 1B a section along the line A-A of FIG. 1A and FIG. 1C a detail of the portion B marked in FIG. 1B;

FIG. 2A is a side and partial section view of an olive in accordance with the present teaching and FIG. 2B is a top view of the same device;

FIG. 5 is a perspective view from above of another olive in accordance with the present teaching;

FIG. 6A is a section through a portion of an olive with a distributed air feed;

FIG. 6B shows a plurality of air channels that may be used with the air feed of FIG. 6A;

FIG. 6C is a perspective view from above of the olive of FIGS. 6A and 6B and shows detail of a suture winder component of an olive in accordance with the present teaching;

FIG. 13A is a side view of a an olive provided in accordance with the present teaching being used in conjunction with a trocar;

FIG. 13B shows a front elevation view of the device from FIG. 13A;

FIGS. 13C-13D show a section view of the device from FIGS. 13A and 13B in tissue and illustrates how the device may be used to close the wound once the trocar and olive are removed;

FIGS. 13E to 13G show another example of an olive provided in accordance with the present teaching being used in conjunction with a trocar and suture to close a wound;

FIGS. 21A through 21H show examples of anchors that may be provided in accordance with the present teaching.

DETAILED DESCRIPTION OF THE DRAWINGS

Figure 3:
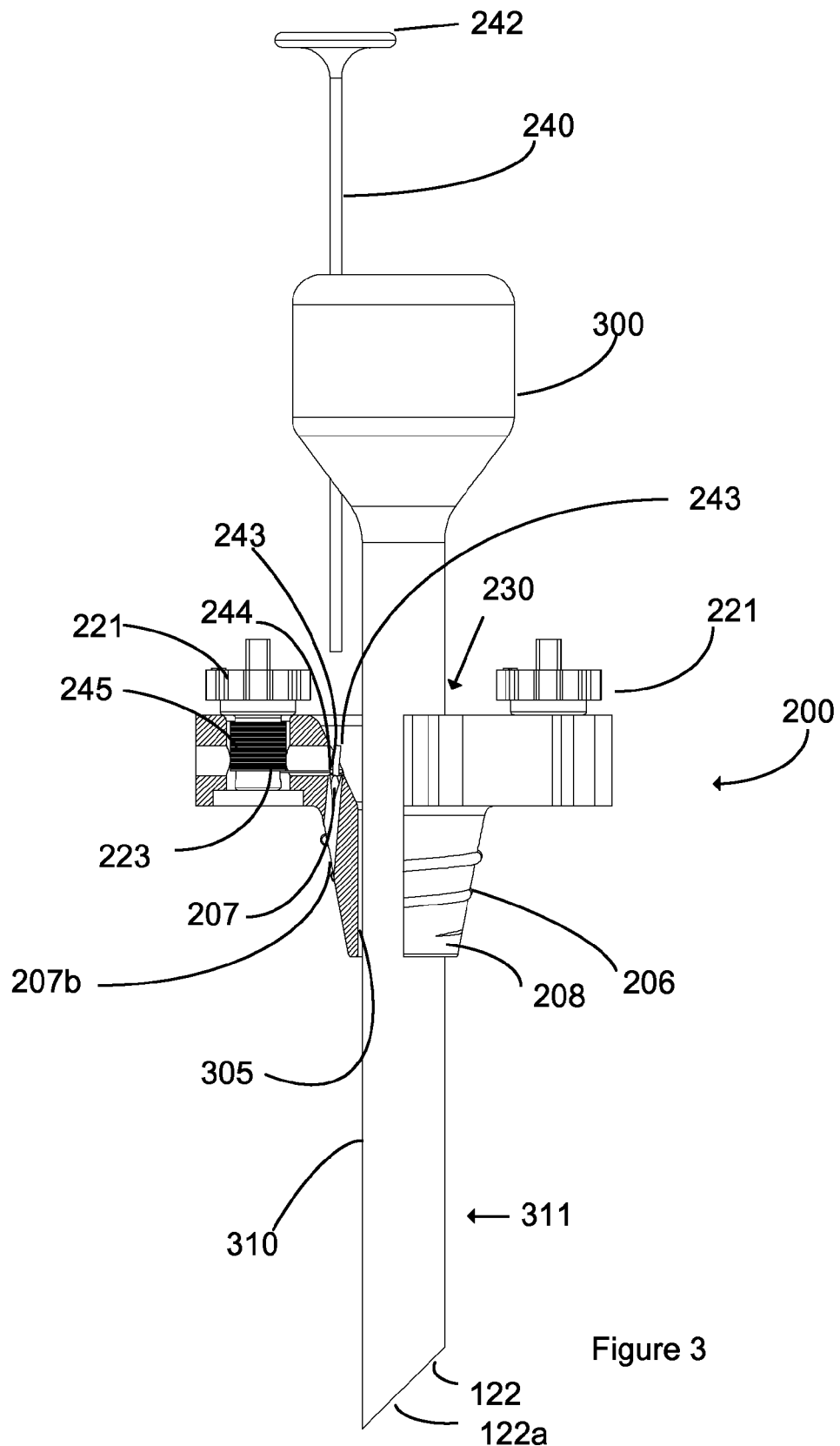
FIG. 3 shows the device of FIG. 2 used with an exemplary trocar.

The teaching of the present invention will now be described with reference to exemplary embodiments thereof which are provided to assist with an understanding of the invention and are not to be construed as limiting in any way. It will be appreciated that modifications can be made to the exemplary arrangements which follow without departing from the scope of the invention which is only to be limited insofar as is deemed necessary in the light of the appended claims.

FIG. 1 shows a trocar 100 in accordance with the present teaching. The trocar 100 comprises a sleeve or shaft 120 defining a hollow interior. The sleeve 120 comprises a substantially cylindrical form having a proximal end 121 and a distal end 122 which is located in the wound during use. The sleeve 120 comprises at least a first tissue slot or window 125 formed as an opening in the cylindrical trocar wall 126 and allowing access to the interior volume of the trocar. In this exemplary arrangement first and second slots are provided and are formed at diametrically opposite locations to each other on the cylindrical wall. The slots 125 are located towards the distal end of the sleeve so as to provide modes of operation of the trocar which allow the slots to be coincident with the abdominal wall when the trocar is inserted through the wall and the distal end 122 enters into the abdominal cavity. The distal end 122 may be provided with a sharpened end surface 122a to assist in the penetration of the trocar through the abdominal wall.

The trocar is configured in this exemplary arrangement for use with a co-operating obturator 140 to allow for a closure of a wound post-surgery. The obturator is configured to be receivable within the trocar and has a side wall 141 with an outside diameter substantially comparable with an inner diameter of the trocar side wall 126. The obturator 140 is also desirably hollow. The side wall 141 of the obturator desirably terminates with an atraumatic tip 142 so as to not damage tissue on contact therewith.

The obturator 140 desirably also comprises at least one window 144, desirably two, provided in the side wall 141 of the obturator. The windows 144 are desirably located such that when the obturator is received within the trocar, the windows of the obturator are not coincident with the windows of the trocar. The windows 144 of the obturator are desirably longer than the windows 125 of the trocar and operably extend further into the abdominal cavity than the windows of the trocar. Rotation of the obturator relative to the trocar will bring the two sets of windows into alignment. In this way, tissue 150 will invaginate through the side walls of each of the trocar and the obturator and will be received into the interior volume 145 of the obturator.

In use, the obturator and trocar are co-operable to provide closure of an opening in the abdominal wall subsequent to a laparoscopic surgical procedure. The obturator desirably has a length greater than that of the trocar to allow for its presentation into the interior volume of the trocar shaft and extension into the abdominal cavity. To facilitate control of the obturator it may be provided with a handle (not shown) at a proximal end thereof for control of the location of the obturator in the trocar.

The trocar and obturator collectively provide a suture closure system. First and second needle slots 130 are defined in the trocar side wall and extend downwardly from the proximal end 121 of the device towards the windows 125 that are defined in the side wall. The slots are dimensioned to receive a first and second needle respectively. The slots extend in an orientation that is substantially parallel with the longitudinal axis of the trocar. The slots 130 terminate at an upper surface 131 of the trocar window 125. In use, subsequent to presentation of the trocar and obturator into the abdominal wall, a needle may be passed downwardly through each of the slots 130 and enter into the space defined in the windows 125 in the side walls. Further presentation of the needle downwardly will cause it to deflect against a deflector 132 defined in a lower surface 133 of the trocar window 125. The needle will hit the deflector and be directed inwardly, entering into the interior volume 145 of the obturator through the aligned window 144. The direction of the passage of one exemplary needle is shown by the arrows 135. It will be appreciated that by passing through the windows of each of the trocar and obturator that the needle will pass through the invaginated tissue 150 that is located therein. As the needles are coupled to sutures, the passage of the needles into the obturator volume 145 brings the sutures through the invaginated tissue and into this interior volume. The needles rest inside the obturator, which when retracted pulls the suture ends out of the body. When the trocar is removed, the suture material passes through the suture passage 127, allowing the trocar to be removed while leaving the suture in place.

The trocar and associated obturator may be used in first and second modes of operation. In a first mode of use, the suture closure system is not enabled. In a second mode or the suture mode of use, the suture closure system is enabled.

In the first mode, the obturator is rotated relative to the trocar so that the windows in each are not aligned. In this way, which is usefully employed during presentation of the trocar through the abdominal wall, the tissue windows 125 on the trocar are blocked by the obturator body. Effectively, for insertion, the obturator 140 is located within the sleeve such that planar portions of the cylindrical wall of the obturator 140 are located at the slots 125 to block the slots so that no tissue can encroach within the device.

After insertion, the obturator 140 may then be removed and the trocar shaft may be used as a standard sleeve during the surgical procedure to allow for passage of other surgical devices into the abdominal cavity for use in the surgical procedure as desired. During surgery, the slots or windows 125 do not pose a problem as they are located towards the distal tip 122 of the trocar shaft and there is no risk of the operating devices snagging on it. The location of the slots 125 on the sleeve 120 is also such that during the operation the slots 125 are located beyond the tissue margin and therefore no tissue is invaginated into the slots.

In the second mode of use, the suture closure system is activated. In a first step the trocar shaft 120 is withdrawn to a level where the slots 125 meet the fascia layer FL of tissue and this fascia layer is allowed to invaginate into the slots 125 as shown in FIG. 1C.

The second step in this process is to rotate the obturator 140 relative to the trocar so as to bring the obturator windows into alignment with the trocar windows. This can be communicated to the operator by use of visual indicators on for example upper surfaces of the trocar and obturator or by employing stops which provide a physical indication that the two are aligned. The tissue will then invaginate into the interior volume of the obturator. The needles can then be passed through the tissue as discussed above.

On completion, the obturator is positioned so that its suture passages line up with the trocar needle slots 130, the obturator and needles are then retracted together. The trocar is then removed. The operator is now left with two suture ends (one per needle) which have been passed through tissue and then out of the abdominal wall. Tightening of each of the two ends will cause the tissue to be contracted, closing the wound. The surgeon will then use the provided suture ends to suture the wound closed ensuring that the fascial layers of tissue at either side of the wound are proximated.

FIG. 2 shows a self-anchoring olive arrangement 200 for use in laparoscopic surgery. As shown, a housing which in this exemplary arrangement is provided in the form of an olive 200 is provided which in use may be anchored to an abdominal wall to define an entry port for presentation of a trocar or surgical devices into the abdominal wall for enabling laparoscopic surgical procedures. The words "olive" and "housing" within the context of the present teaching may be used interchangeably. The olive 200 comprises an abdominal wall piercing or engaging portion 205 and an outer resting portion 210 which in use will rest against the outer surface of the abdominal wall. In this exemplary arrangement the abdominal wall engaging portion 205 extends inwardly from the resting portion and is defined by a hollow conical structure having side walls 205a that taper inwardly. Threads 206 are arranged about the side walls 205 and operably provide for an anchoring of the olive against the abdominal wall. In this exemplary arrangement the threads are configured to helically extend about the outside surface of the abdominal wall engaging portion 205. These helical threads could be inflatable or otherwise expandable so that the cone may be inserted with a lower profile smooth cone. The threads could then be deployed to anchor the olive in position. The threads could also run in a non helical fashion, such as linearly descending to avoid conflict with the guide channel 207, or extend inwardly such that on their expansion would effect a downward movement of the olive.

The abdominal wall engaging portion or insertion cone 205 is desirably provided at a mid-point of the olive 200 such that the outer resting portion is arranged symmetrically about it. The resting portion desirably has an inner surface 211 which in use will be proximal to and intimately resting on the outer surface of the abdominal cavity. An outer surface 212 is spaced sufficiently apart from the inner surface 211 to allow for location of a suture winding system 220 within the body 213 of the outer resting portion 210. The olive 200 defines an aperture in the body of the outer resting portion 210 that extends through to the abdominal wall engaging portion so as to define a lumen 230 for allowing introduction of a trocar into the abdominal cavity. An insufflation port could be incorporated into the olive body which, when coupled with a sacrificial breakaway seal over the lumen 230, would enable insufflation of the abdominal cavity prior and independent to trocar entry. In this embodiment, a pivotable or deformable conical tip may be incorporated into the abdominal wall engaging portion to enable insertion without a trocar or obturator.

The suture winding system 220 in this exemplary arrangement comprises first and second suture winders 221a, 221b provided on the upper surface 212 of the body 213. In this exemplary arrangement they are arranged on opposite sides of the lumen 230. The winders are each mated with a shaft 222 which is coupled to a spool 223. Rotation of the winders effects a corresponding rotation of the spool 223. On each spool a length of suture is wound. For each spool 223, a suture aperture 224 is provided, the suture aperture 224 providing for passage of the suture from the spool to a needle guide channel 207 provided in a side wall of the abdominal wall engaging portion 205. The needle guide channel 207 provides an entry port for a needle to pass from an inner surface 209 of the abdominal wall engaging portion 205 through the olive to exit through a needle tip exit hole or exit port 207 provided on the outer surface 208 of the abdominal wall engaging portion 205. The needle guide channel is desirably configured to taper outwardly such that a needle presented through the guide will be directed into the abdominal wall that is contacting the abdominal wall engaging portion 205. The anchors exit at a fixed angle which may be optimally configured between 5 and 30°, or more preferably between 10 and 20°.

By providing the suture apertures 224, suture from the winders can be coupled to respective needles and directed into the abdominal wall. The needle is desirably biased inwardly through the guide 207 using a needle driver 240 having a shaft 241 and a suture press 242 by which an operator may apply a downward pressure onto a needle 243 located in the guide 207. The exit hole 207 is desirably located such that the needle will pass into the subcutaneous layer of the abdominal wall. Desirably application of continued downward pressure using the needle driver 240 will cause the needle 243 to then pass into the abdominal cavity, pulling the deployed suture with it. In this deployment configuration, each of the spools is free to rotate so as to allow a controlled release of suture from their respective spools 223. Additionally the length of the needle driver can be sized such that when fully extended, suture still remains on the spool, ensuring that the user will have adequate suture to make the closure knot.

On passage of the needle into the abdominal cavity it will desirably hang, suspended on its suture after the suture press is removed. The orientation of the needle will typically change orientation from a vertical disposition used in the deployment configuration to a horizontal configuration. This may be assisted by coupling the suture to the needle 243 at a mid-point 244 such that it will pivot relative to the coupling to change its orientation. The side of the needle 243 then provides a contact surface 245, which can be used to anchor the olive against the inner abdominal wall. In this preferred arrangement this anchoring is effected by retracting the deployed suture using the suture winder 221 to wind the suture onto its spool. This causes the suture to be pulled back into the olive, tightening the needle against the inner abdominal wall. As the orientation of the needle has changed, it will not tend to retreat back through the abdominal wall through the path it developed on penetration of the wall. The olive is then resting against the outer surface of the abdominal wall through contact of the inner surface 211 against the abdominal surface and is prevented from moving away from that position through the action of the needles against the inner surface of the abdominal wall. It is self-anchored.

Desirably the suture winders 221 may be provided with a locked and unlocked position which may be indicated to the operator through use of visual indicators 250, 251 respectively provided on an upper surface 252 of the suture winder. The operator will typically use the unlocked orientation to allow for the free deployment and retraction of suture. It may then change the winder to a locked configured to prevent further release or retraction of suture. This will desirably be adopted on achieving the anchored position.

The suture winder may comprise clutches to control the tension that may be applied to the suture on retraction of the suture onto its winder. Each of the two described winders may have their own clutches in for example the form of a roller clutch. In a desired configuration first and second roller clutches may be provided on each winder so as to allow for each winder to retract to a different position relative to the other, controlling the direction of drive transmission. Alternatively, a spring plunger could be used to engage with indexed indentations on an annular ring placed over the spool pin or on the spool pin itself, and slip from one indentation to the next when the suture is tightened to a predetermined limit, giving the user an indication that the suture is fully retracted.

It will be appreciated that this anchoring may take some time. To provide for a temporary location of the olive adhesive pads may be provided on the lower surface 211 which will temporarily bond with the surface of the body and allow for the deployment of the needles to adopt a more permanent secondary anchoring.

On completion of the surgical procedure, the deployed needles and sutures may be used to effect a closure of the wound. The spools are unlocked and the olive is retracted from the abdomen. The unlocked spools allow additional suture to be released from the spools as the olive is withdrawn. When sufficient suture is available the surgeon may then cut the suture, tie a knot, and use the still tethered suture to effect a closure of the wound. Desirably sutures and/or needle anchors are bioabsorbable so as to allow for their eventual dissolving after the procedure.

An alternative method of use would be to deploy the needles as described above. To close the wound the needles could be picked by a grasper disposed through the trocar while the spools are in the unlocked position. The anchors are removed through the trocar; the two suture ends are tied or mated and passed through the trocar again to create a closed loop of suture. This joining process could also be completed internally. The olive would then be removed and the suture trimmed and knotted as described above.

It will be appreciated that FIG. 2 provides an exemplary arrangement of a suture anchoring system that employs sutures that are wrapped around spools provided within an olive, the suture being coupled to a needle/anchor located at their proximal ends. The sutures run across a needle access port which runs obliquely to the vertical axis of the device to guide needles through the fascial layer of the abdominal wall. While the helical thread was not described as being bladed, a bladed thread may also be incorporated into the funnel or conical portion of the device to enable initial anchoring of the device prior to insufflating the peritoneum. After insufflation the needles are driven through the fascial layer. The needles then pivot and anchor the device when the spool is rotated to retract the suture. A push button mechanism or secondary rotary mechanism may then be used to lock the suture, anchoring the device. At the end of the surgery the spools are unlocked and the device withdrawn. The user is then left with two sutures which may be tied to close the wound. While described with reference to two spools it will be appreciated that this is provided to assist in an understanding of the present teaching and should not be construed as being limited in that more spools may be used if required.

The device in this embodiment is at least twice as wide as it is deep. This is an important feature as it enables the device to rotate in situ prior to anchoring. It will be appreciated that the longer the length of the insertion cone 205 the less freedom a surgeon has during the laparoscopic procedure to manipulate his laparoscopic tools which are accessing the internal cavity through the device. In this way by maintaining the insertion cone 205 as a shallow element more freedom is provided to the surgeon.

In the exemplary arrangement of FIG. 2, the needle driver was provided as a separate element. FIG. 3 shows a modification where the same reference numerals are used for similar components. In the arrangement of FIG. 3, a trocar 300 is provided with is receivable through the lumen 230 of the olive 200. The inner walls of the abdominal wall engaging portion 205 may be configured to be parallel with the outer surfaces 208 or may include a portion 305 which is configured to be substantially parallel with the vertical axis of the lumen 230. In this latter configuration in this region, on introduction of the trocar into the olive an outer surface 310 of the trocar shaft 311 is substantially parallel with the inner surfaces of the lumen. The spacings between each are desirably sized such as to minimise any rocking of the trocar shaft within the lumen 230. An interference fit or a semi rigid olive portion 208 may be utilized to maintain an air tight seal between the olive and trocar shaft.

The needle driver 240 is integrated in this configuration into the trocar, such that the trocar provides a guide for the needle driver. In the arrangement illustrated a single needle driver is provided such that deployment of the first and second needles will have to be done sequentially. To achieve this, the needle driver would be presented through the trocar and contact the needle within the needle guide. Force acting downwardly would cause the needle to be deployed from the guide. The needle driver would then be presented to the second needle on the opposite side of the lumen. To obviate the need for individual needle deployment, the trocar could be provided with first and second needle drivers to allow concurrent deployment of both needles. This process could be further simplified by locking both needle drivers to a common driving element such that a single action caused both needle drivers to be actuated concurrently.

Figure 4A:
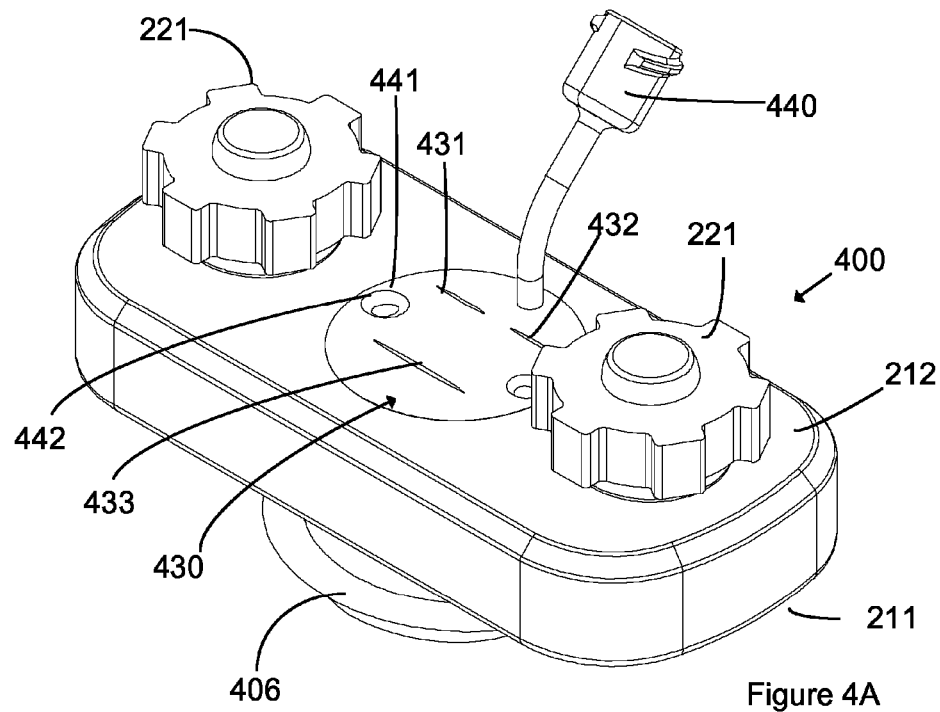
FIG. 4A is a perspective view from above of a modified olive in accordance with the present teaching and FIG. 4B is a partial section through the olive of FIG. 4A.
Figure 4B:
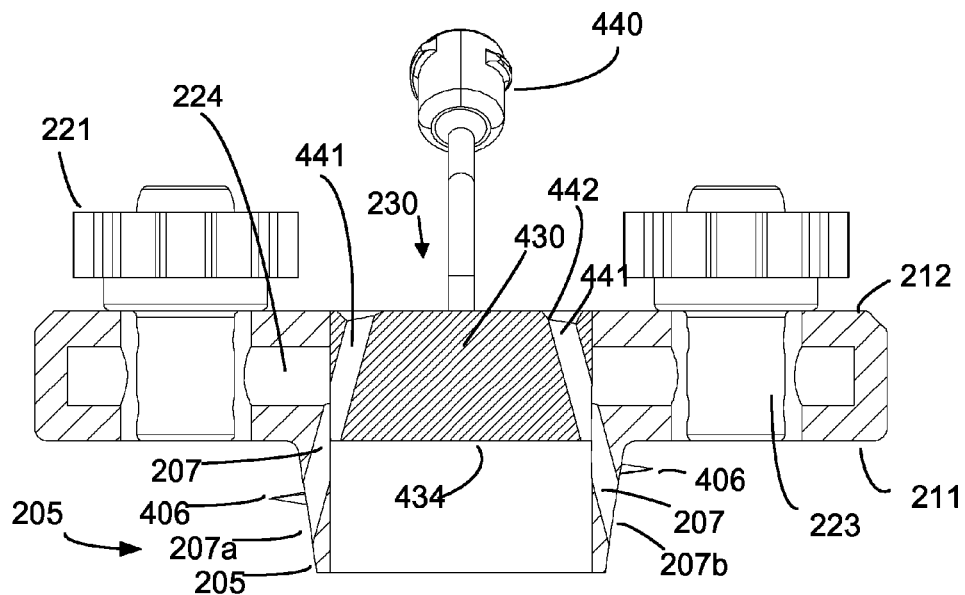

FIG. 4 shows a further modification designed for single port surgery whereby the abdominal wall engaging portion 205 is not provided with a helical thread such as described above but rather with a bladed thread 406. The bladed thread is again used to anchor the olive 400 within the abdominal wall. The abdominal wall engaging portion 205 is again chosen to have a length that is not sufficiently great as to project a substantial distance into the abdominal cavity during use.

In this configuration the lumen 230 is filled with or formed from an elastomeric material 430 which provides for a sealing of the abdominal cavity during the surgical procedures. The specifics of the material used may vary depending on the desired level of flexibility required. For example, the port material may be fabricated from a polyurethane hydrogel such as HydroThane™ hydrophilic thermoplastic polyurethanes that may be configured to expand on exposure to a saline solution so as to both provide lubrication and improved seal. The elastomeric material may be manufactured from an oil exuding silicone for example NuSil™ MED-4955. This material can be cast as a solid block with undersized lumens, or tapered slits disposed therein for passage of surgical instruments. The material may exude silicone oil, which would advantageously lubricate surgical instruments inserted through the port. Alternatively the port could be cast from a lower durometer silicone dispersion eg NuSil™ MED-4011 and be coated with silicone oil eg NuSil™ MED-400. Any of the following silicone dispersions could also be used with silicone oil; MED-4044, MED2-4220, MED4-4220, MED-4920 or MED4930 [all NuSil™]. The elastomeric material may be reinforced with a woven mesh or thin film, which may be porous in nature, on its top and bottom surfaces or indeed about its complete perimeter. Use of such a mesh or film would be particularly useful for gel port or very low durometer configurations. This elastomeric component may be provided with one or more slits or openings on its top surface to facilitate device placement.

The elastomeric material could also be manufactured from an open cell polyurethane foam or fast acting viscoelastic foam. The polyurethane foam will have a skin either integrally formed or by addition of a polyurethane sheet which may be solvent bonded or otherwise attached to the foam. Slits or holes may be cut into the foam, as entry points for surgical instruments. The foam may be loaded in compression to improve its performance as an air barrier, maintaining insufflation of the abdominal cavity. In this embodiment the polyurethane foam may be loaded with silicone oil eg NuSil™ MED-400 or other lubricant, which will ensure smooth movement of surgical instruments through the port.

It will be understood that despite the desire to provide a sealed arrangement it is also necessary to allow the passage of surgical devices through the olive 400 into the abdominal cavity. In the example of FIG. 4 three slits 431, 432, 433 are provided through the elastomeric material 430. The elastomeric material 430 which provides an access platform is desirably fabricated from a low durometer (shore hardness 0-50 A) polymer which features slits sized to suit 2×5 mm and 1×10 mm devices. The slit depth tapers inward to create a seal that may be broken on inserting a device through the slit. The taper may run through a portion of or through the complete depth of the slit which could embody a cross hair or single axis geometry. The access platform may also be loaded in compression to enable better sealing. Silicone or silicone based elastomers, santoprene, or thermoplastic polyurethanes would be advantageous for this application.

As was mentioned above, each of the three slits are dimensioned to receive specific surgical devices. As is shown in FIG. 4, first and second slits 431, 432 may be dimensioned smaller than a third slit 433. In this way the surgeon is provided with alternatives as to the appropriate slit to use for a specific tool. The elastomeric material section may also be rotatable in certain configurations. In the arrangement of FIG. 4 the first and second slits are configured to receive devices of 5 mm diameter whereas the third is configured for use with 10 mm devices. The device entry slits 431, 432, 433 may taper to a closed profile on an inner surface 434. The elastomeric material 430 which may be provided in the form of a gel may also be configured to receive an insufflation port 440 through which the abdominal cavity may be inflated to a desired pressure. The material may also comprise needle driver guide channels 441 which are located relative to the needle guide 207 to allow for a passage of the needle driver 240 therethrough. The needle driver guide channels 441 may be provided with tapered lead in surfaces 442 to facilitate the presentation and introduction of the needle driver into the guide channels 441.

In the arrangement of FIG. 4, the insufflation port 440 accesses the olive through the elastomeric material 430, i.e. it is coupled through the upper surface 212 of the olive 400. In a modification, shown in FIG. 5, the port 440 is coupled through a side wall 500 of the olive. This provides more space on the upper surface, specifically in the region of the elastomeric material 430. In this way, during use of the olive, the surgeon does not have the port occupying the field of view of the upper surface of the olive 400. Two insufflation ports may be provided to enable insufflation gas filtering and circulation.

FIGS. 6A through 6C show an exemplary arrangement whereby the air that is introduced by the insufflation port 440 may be routed through to the abdominal cavity. In this arrangement, the insufflation port is coupled to a side wall 500 of the olive and air provided through the port enters via an entrance port 601 provided on an inner surface. The air is routed to a plurality of vertical channels 602 via an annular air channel 603 that is coupled at a first end to the entrance port 601 and at the second end to each of the plurality of channels 602. The channels are disposed about the perimeter of the lumen 230 and each terminates in an air exit aperture 604. By providing a high pressure source of air from the insufflation port a screen of air will be generated across the lumen 230 coincident with the exit apertures 604. Depending on the relative orientation of each of the apertures to one another this may be in the form of a horizontal screen. By suitably arranging the pattern and number of channels it is possible to preferentially direct the air inwardly from one side of the lumen as opposed to a second different side. For example, the vertical channels could be provided on one side only of the lumen and direct air across the diameter of the lumen from that one side.

The air screen that is thus generated creates a pressure barrier across the lumen that may prevent the passage of ambient air inwardly into the abdominal cavity. Such an arrangement could be used in combination with the elastomeric material 430 described above with reference to FIGS. 4 and 5 or could be used without such a physical barrier—as shown in the schematics of FIG. 6. It will be appreciated that such an arrangement utilizes a high pressure flow to create an air barrier to create a seal over the pneumoperitoneum which eliminates the requirement for the combi-gel port of FIGS. 4 and 5. An inlet and outlet may be used in this configuration to facilitate filtering of gas within the pneumoperitoneum.

FIG. 6 also shows a modification to the spool winder 221 where first and second holes 610 are provided on winder shaft 611 to facilitate the knotting of a suture in order to fix the suture to the spool winder.

FIGS. 7A-7D show a further port 700 that may be used in laparoscopic surgery in accordance with the present teaching. This port is specifically configured for use as a single incision laparoscopic surgery (SILS) port and addresses problems associated with conventional SILS ports. Specifically with conventional ports, one limitation of current devices is their difficulty of insertion and that the bulk of the device rests on the outside surface of the abdomen. This bulk obstructs the working angle of the instruments being advanced through the port and can make it more difficult to reach the target organ.

As shown in FIG. 7 in this exemplary arrangement a port 700 comprises first 710 and second 720 rings that are coupled to a flexible elastomeric sheath 730. The sheath is dimensioned to adopt a conical form when extended. It is coupled at a first end 731 to the second ring 720 and at a second distal end 732 to an anchor element 740. The anchor element 740 has first and second tabs 741, 742 that project outwardly on opposite sides of the sheath 730. The anchor tabs may also be provided in a predefined inflatable geometry which would enable lower profile entry through the incision.

Figure 7A:
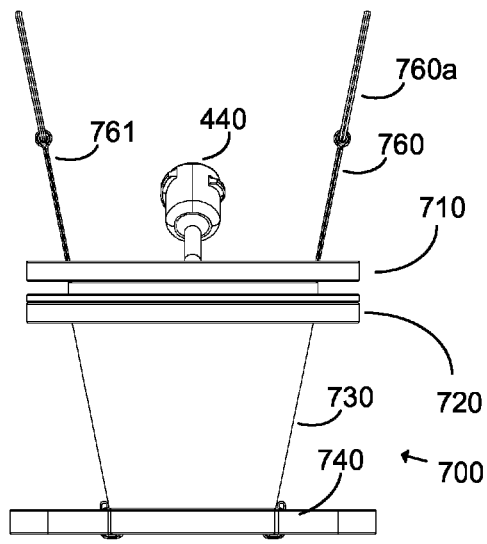
FIG. 7 shows an example of a port closure system in accordance with the present teaching.
Figure 7B:
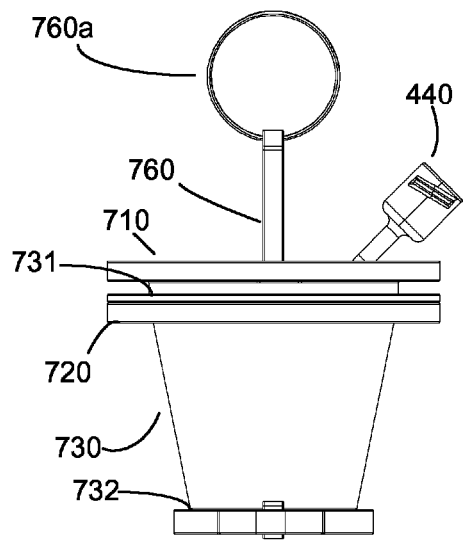
Figure 7D:
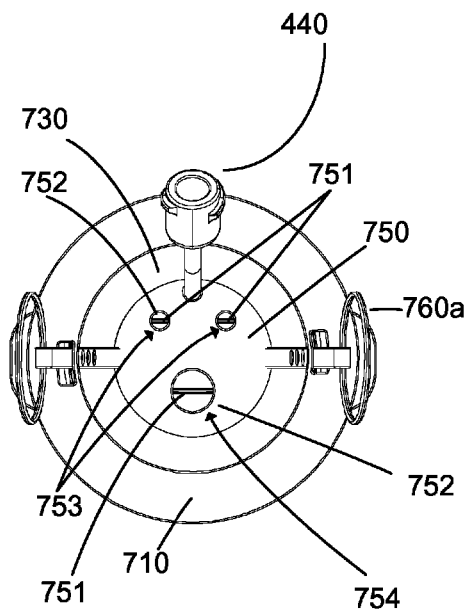
Figure 7C:
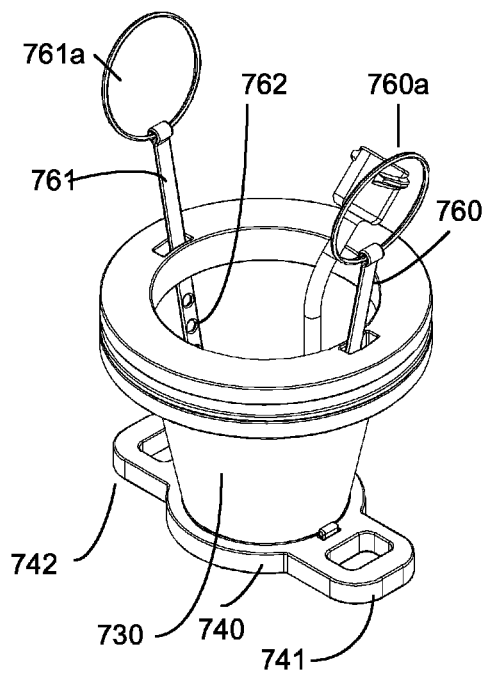

The port 700 features inner abdominal level access which brings the device access point closer to the target organs, this also minimizes the profile on the outer abdominal wall to increase the degrees of freedom of device movement on the outside. As shown in FIG. 7D this may be provided by having an access layer 750 provided across the elastomeric sheath 730 coincident with the distal end 732 of the sheet 730. The access layer 750 is desirably formed in two-part seal construction with a top 0.25-1 mm elastomeric layer provided above a bottom layer (2-10 mm) formed from a low durometer flexible material which self seals after device removal. The top layer may be provided in a transparent or translucent material to allow the operator to see through the layer. This top layer may be integral with and formed from the same material as used for the remainder of the elastomeric sheath 730.

Each of the top and bottom layers are provided with apertures to allow surgical device access to the abdominal cavity. In this exemplary configuration three slits or apertures are provided, similar to what was described above with reference to FIG. 5 with two apertures 753 providing access ports for smaller diameter surgical devices than a third aperture 754.

In this configuration the top layer aperture 752 is sized to be at least 50% smaller than target device and the bottom layer slit 751 is sized to be shorter than the target device diameter. An insufflation port 440 is also provided with access through the access layer 750.

It will be appreciated that as the sheath 730 is provided as a flexible material that it may be collapsed in onto itself so as to allow the anchor element to be brought into intimate contact with one or both sides of the lower ring 720.

One or more holes 762 may be provided in the straps 760 to facilitate the passing of a suture therethrough. Pull-rings 760a and 761a may be provided on each of the straps to assist in the retraction of the straps. An example of how the device may be used is as follows:
  (a) Cut through the abdominal tissue until access to the abdominal cavity is achieved.
  (b) Grasp the anchor 740 at one of the two tab portions 741, 742 with a conventional grasper and drive through the tissue until the first (grasped) edge 741 of the anchor is positioned within the peritoneal cavity. It is important to drive the anchor edge parallel to the incision to ensure that provided incision retraction straps 760, 761 are correctly aligned for optimum retraction.
  (c) Grasp and position the second edge of the anchor inside the peritoneal cavity, the elastomeric sheath stretches to accommodate different abdominal wall thicknesses.
  (d) Retract the incision by pulling the incision retraction straps. It will be appreciated that as the anchor is abutting against the inner abdominal wall, that a retraction of the straps 760, 761 effects an extension of the sheath 730 causing an expansion of the incision to adopt a desired diameter. When the desired level of incision retraction is achieved, the upper ring 710 may be pushed downwardly towards the lower ring 720 to achieve a mating with and locking of the retraction straps in their adopted configuration.
  (e) Insufflate. At this stage the insufflation port may be used to effect an inflation of the abdominal cavity.

As discussed above, the port 700 features a two component seal. The first seal is made from an elastomeric material sized to be at least 50% smaller in diameter than the device intended to be inserted through it, so for a 5 mm port the diameter of the hole in the elastomeric sleeve will be at least 2.5 mm. The sleeve therefore becomes a seal when an oversized instrument is passed through it. This sleeve may comprise a thin layer of elastomeric material. Thermoplastic elastomers such as santoprene or EDPM may be effectively utilised for this component. The second seal is fabricated from a self sealing gel port as previously described in the detailed description of FIG. 4. This seal, when broken, allows access to the inner abdominal space and the first seal seals against the device being inserted. The gel port may feature slits which are typically undersized relative to instrument being provided therethrough. For example for a 5 mm device the slit will be typically be of the order of 2.5-5 mm long. The slit is designed to enable easier sealing of the gel port and easier insertion of the device. The slit may taper from its inner surface outward to further ease insertion. The anchor edges can also be configured to receive the grasper to facilitate easier insertion and to ensure a less traumatic entry. This device also enables direct visualization of the fascial layer by utilizing a translucent elastomeric sheath 730. This will facilitate easier closure of the incision by enabling the accurate placement of anchored sutures prior to device removal, which can be tied thereafter to close the incision. The insufflation port may also be incorporated into one of the incision retraction straps to free up space in the access channel.

While devices in FIGS. 4, 5 and 7 are described as having three ports it should be understood that this is not intended to limit the design as versions could be made with additional ports for use in SILS applications.

Figures 8A, 8B:
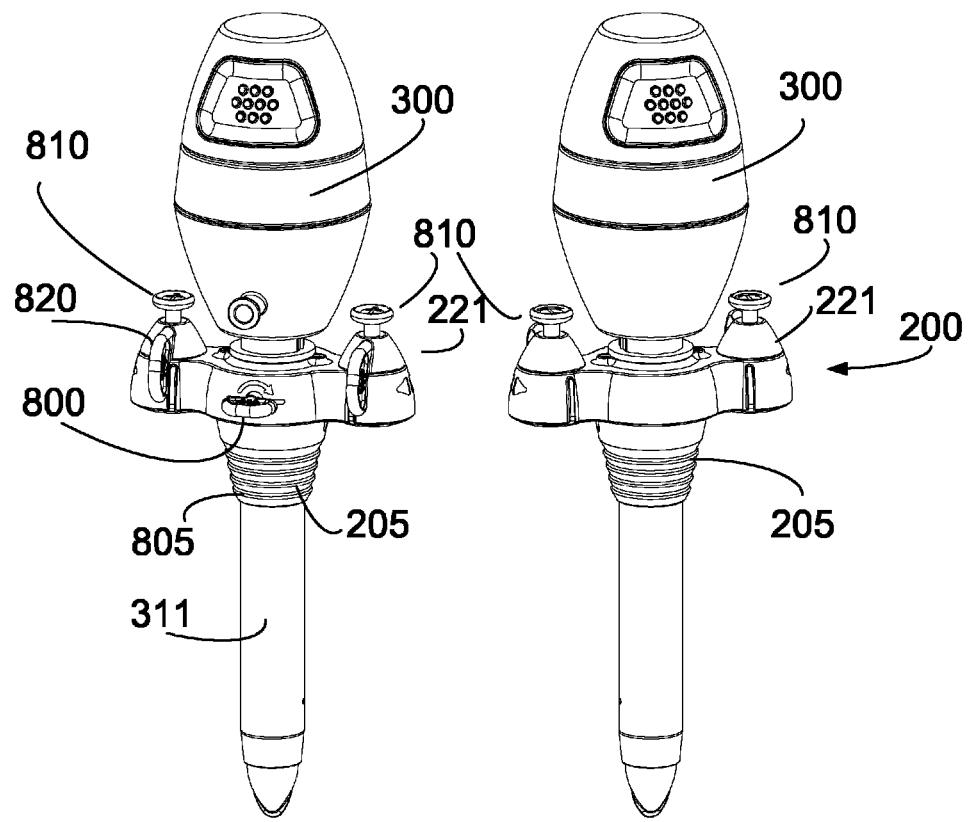
FIG. 8 is a perspective view of a device in accordance with the present teaching with FIG. 8A showing a view from a first side and FIG. 8B a view from a second side.

FIG. 8 shows an olive with a trocar located therein. In this exemplary configuration the trocar 300 may be locked relative to the olive using a locking mechanism 800 such as the exemplary rotary lock illustrated. It will be appreciated that such a lock enables a relative securing of the trocar to the olive to prevent relative movement between the two. In this exemplary configuration the locking mechanism 800 is engaged through movement of a switch through 180°. This will be understood as exemplary of the type of locking mechanism.

The abdominal wall engaging portion 205 is formed in this arrangement from a semi-rigid and ribbed insertion cone. Ribs 805 are provided in a horizontal configuration arranged one above the other on the outer surface of the cone and serve to prevent the olive 200 slipping outwardly once inserted into the incision site. The semi rigid nature of the insertion cone will facilitate an air tight seal between the trocar and olive.

The suture winder 221 may be locked using a push-button locking mechanism 810 which is moveable in a vertical direction parallel to the shaft 311 of the trocar. Retraction of the suture onto its spool is enabled through use of a push button actuator 820 that may utilise a ratchet mechanism to translate the external movement of the actuator to a winding of the suture on its spool.

Figures 9A, 9B:
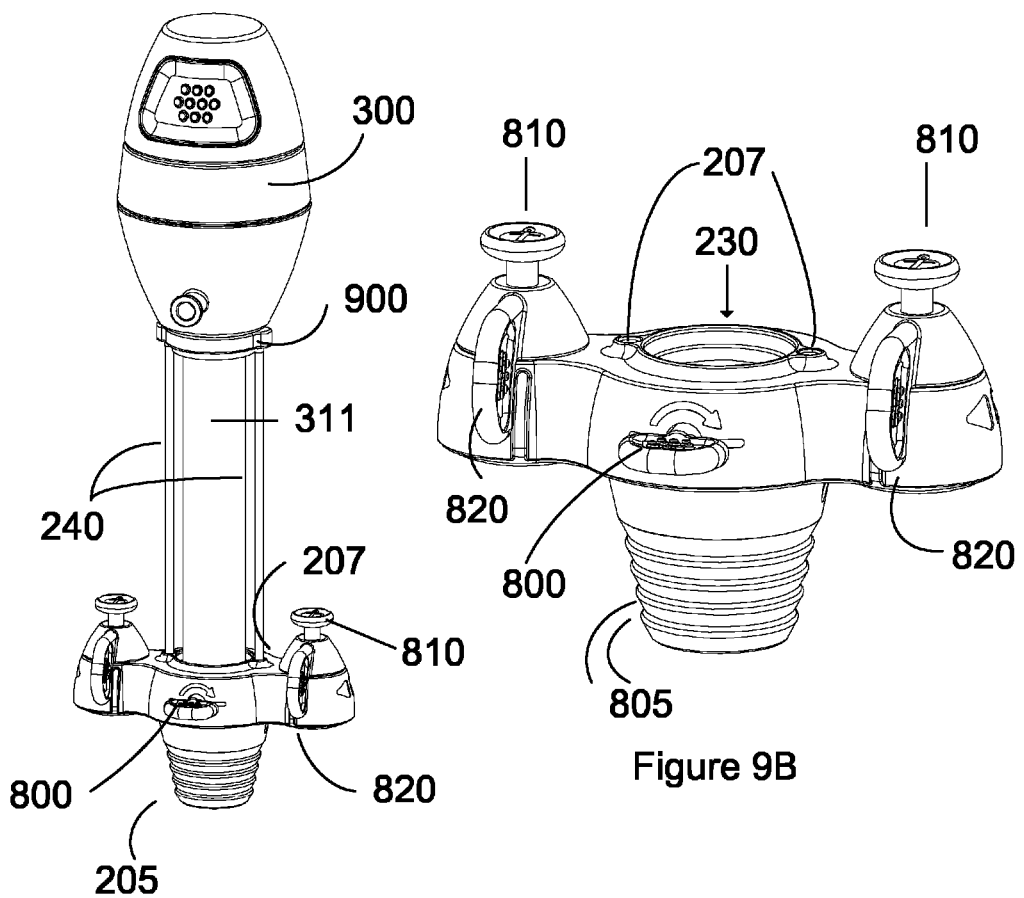
FIG. 9 shows a snap-on needle delivery system for retro-fitting to existing trocars with FIG. 9A showing the system fitted to a trocar shaft and FIG. 9B a detail of an upper surface of an olive of the system showing the entry points for needle or anchor pushing rods.

FIG. 9 shows a trocar assembly similar to that described with reference to FIG. 3 incorporating first and second needle drivers 240 that are located on either side of the trocar. In this exemplary arrangement the needle drivers are provided on a collar 900 that may be retro-fitted to the trocar for use with the olive of the present teaching. In this configuration the trocar and needle drivers are moveable together such that it requires a driving of the trocar downwardly into the olive to effect the corresponding movement of the needle drivers—FIG. 3 it will be recalled described an arrangement where they were independently moveable. In this configuration the entrance port to the guide channels 207 is located on an upper surface of the olive.

An example of how such a system may be used is as follows:

(a) Making an initial incision in the abdominal wall
(b) Providing an olive closure device and trocar as described above with reference to FIG. 9
(c) Inserting the trocar and olive into the incision by pushing the assembly into the incision, ensuring that the suture exit ports are positioned subcutaneously
(d) Locking the olive relative to the trocar using the 180° rotary lock, and insufflating the abdomen.
(e) To move the trocar, the 180° rotary lock is unlocked. The trocar is then used to drive the snap on pushing rods which in turn drive the suture needles inside the abdominal cavity. The snap on pushing rods may then be withdrawn.
(f) Anchoring the olive by tightening the sutures by using the anchor retrieval actuator to take up slack in the suture, drawing the t-shaped suture needles flush against the peritoneum, at which point the anchor lock activation button is activated.
(g) Completing the required surgery, at the end of which the olive is removed by unlocking the anchor lock activation button and lifting it away from the abdominal wall.
(h) Using a scissors or some other cutting tool to cut the sutures close to the olive.
(i) Tie a knot in the suture and pushing the knot subcutaneously.

Figure 10A:
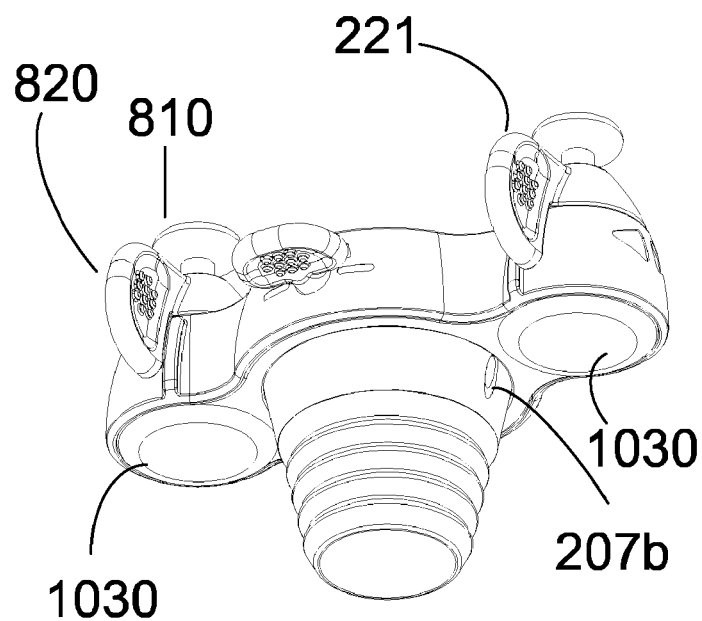
FIG. 10 is an exploded view showing elements of a suture winding system in accordance with the present teaching with FIG. 10A showing a view from below of the olive and FIG. 10B showing internal components of the olive.
Figure 10B:
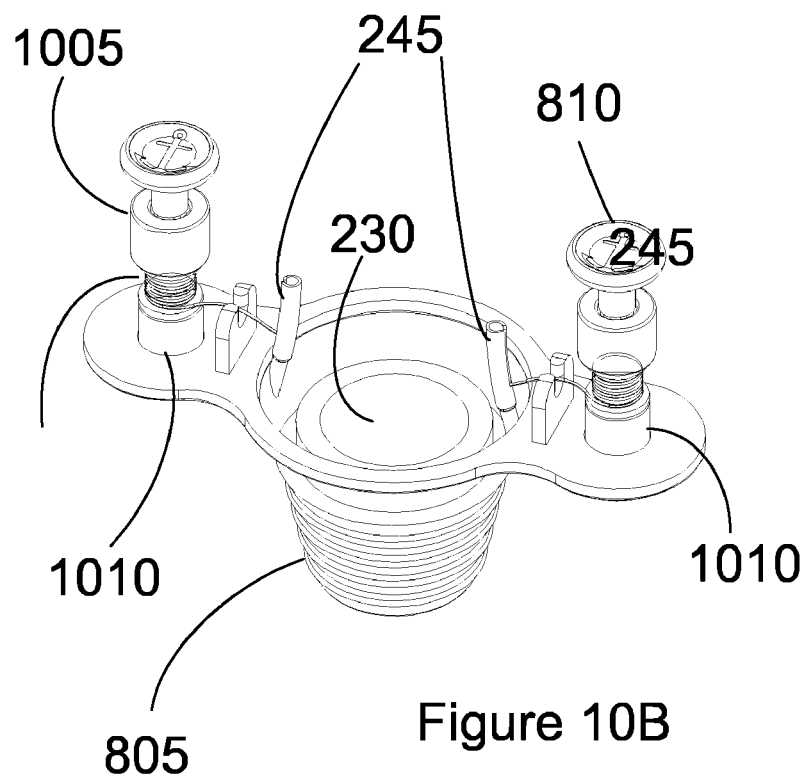

FIG. 10B shows an exploded view of the suture closure mechanism previously described. In this configuration the first and second roller clutches that were mentioned previously are visible. The needles 245 are configured to exit at a fixed angle relative to a vertical axis of the olive which may be optimally configured between 5 and 30°, or more preferably between 10 and 20°

The first roller clutch 1005 is fixed within the actuator 810 of the suture winder 221 which also provides the main drive shaft for the suture winder and enables one directional rotation. The second roller clutch 1010 which is fixed to the olive housing enables rotation in one direction also so that when the drive shaft is moved vertically only one clutch is engaged at a time providing a locking mechanism.

Figures 11A, 11B:
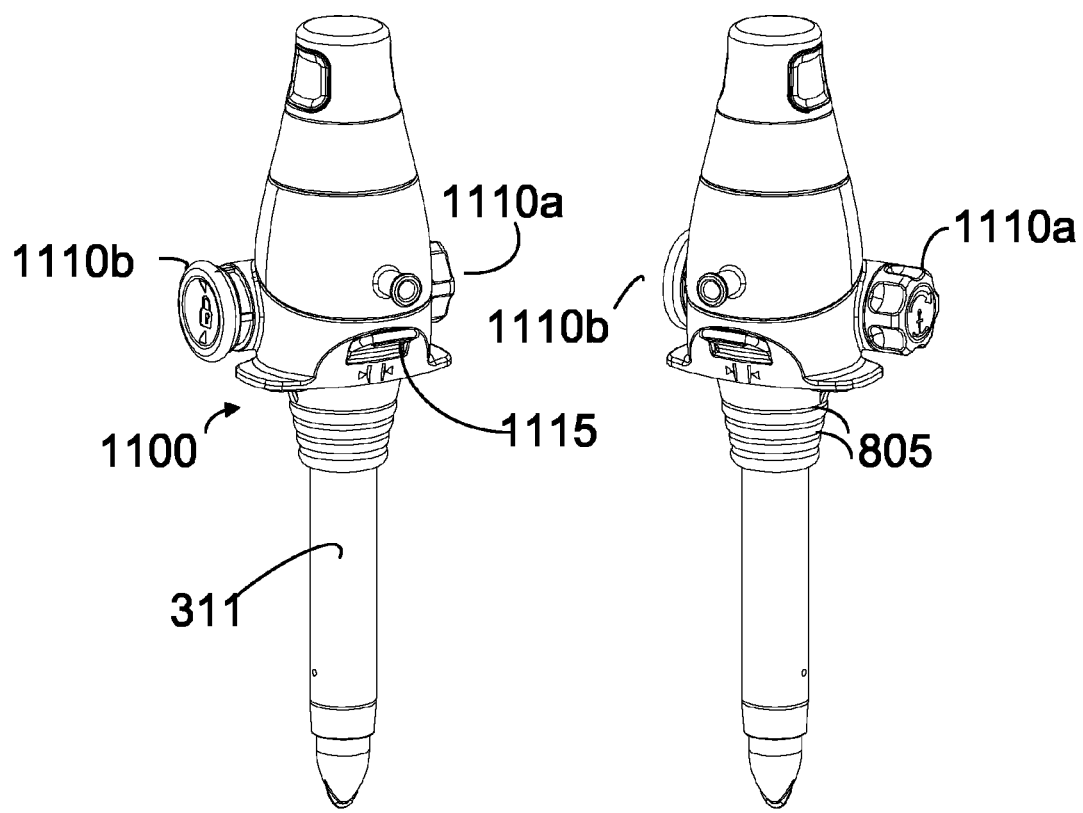
FIG. 11 shows an alternative mounting arrangement for a suture winding system in accordance with the present teaching with FIGS. 11A and 11B showing perspective views from first and second sides, FIG. 11C showing components of the suture winding mechanism utilising a common drive shaft and FIG. 11D showing a view from below of the olive.
Figure 11C:
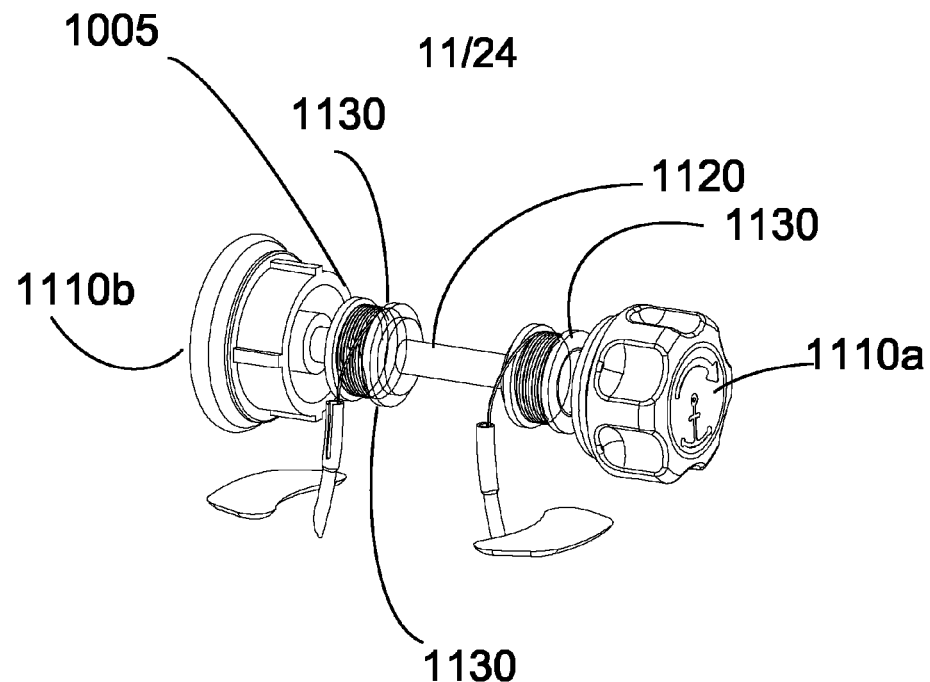
Figure 11D:
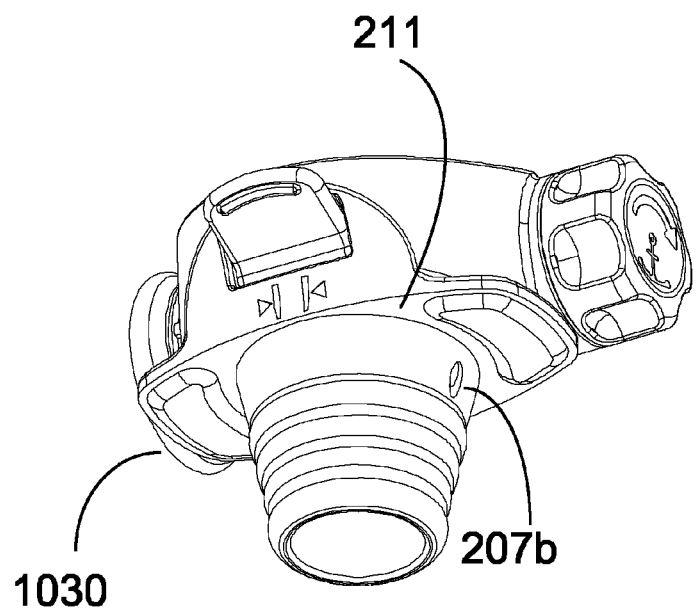

FIG. 11 shows another configuration whereby the orientation of the suture winder is changed so as to act in a vertical as opposed to the horizontal configuration described previously. In this arrangement actuators 1110a and 1110b are provided on either side of the olive 1100. The trocar shaft 311 may be locked in position using a cam lock 1115. The actuators 1110a and 1110b may be arranged to each act independently on a suture spool or each actuator may provide the same function on both spools. For example, a first actuator 1110a may be configured to effect a simultaneous spooling of two or more spools and the function of the second actuator is chosen to provide for simultaneous locking of both spools. An example of how this may be provided is illustrated in the exploded view of FIG. 11C where a common drive shaft 1120 is coupled to first and second spools 1130. The drive shaft may include a spline which interacts with a key on the spool as an alternative method of attaching the spool to the drive shaft.

Figures 12A, 12B:
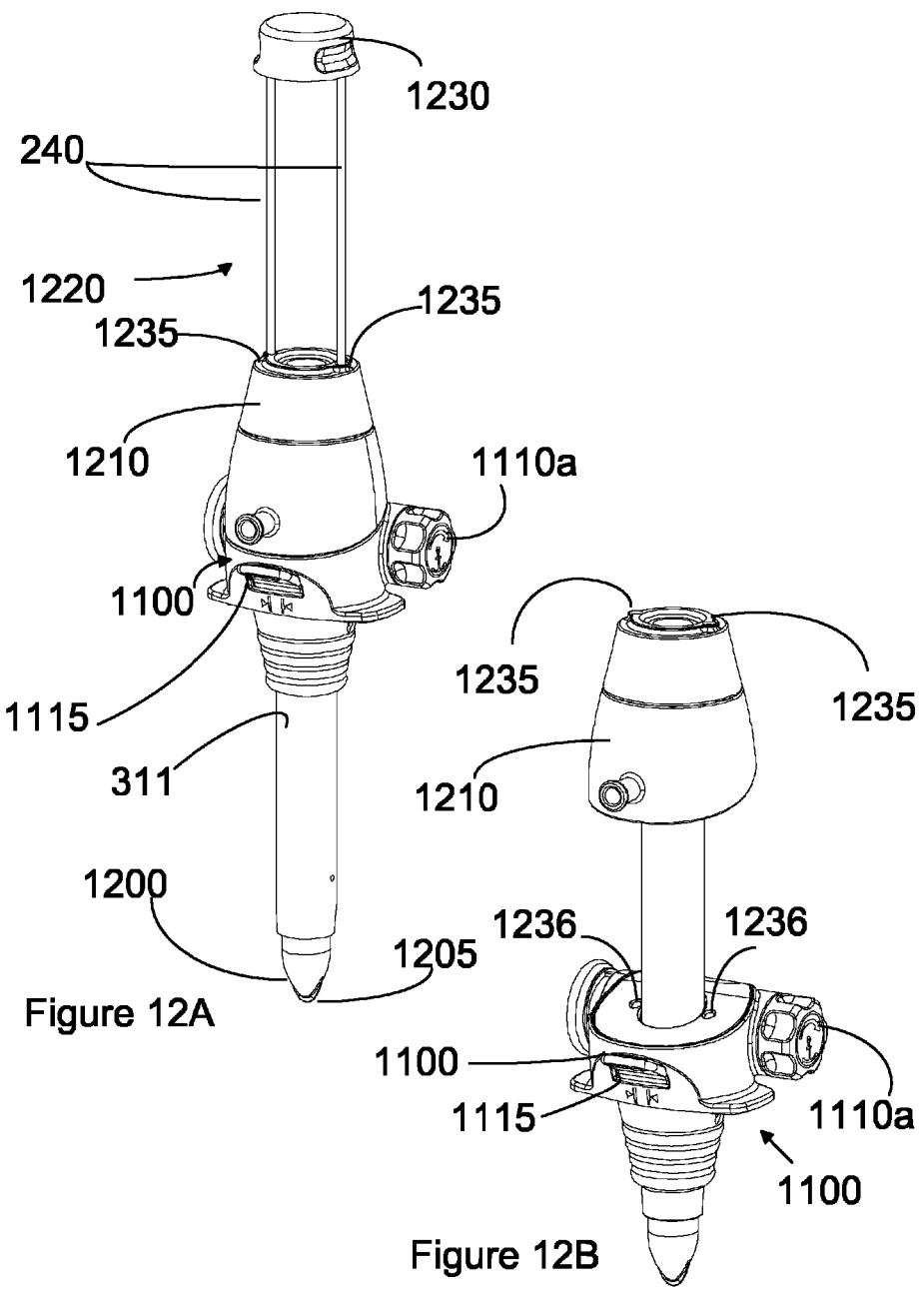
FIG. 12A is a perspective view of a combined trocar/olive device with an anchor deployment tool integrated into the trocar and FIG. 12B shows the device of FIG. 12A with the trocar partially displaced out from the olive.

FIGS. 12A and 12B show another device in accordance with the present teaching. Again the same reference numerals are used for common elements and features. The trocar shaft 311 is again lockable using a cam lock 1115. This may provide a locking indication such as a locking indication for a 45° trocar lock. An obturator 1200 may be provided having a length greater than the trocar shaft 311 so as to allow it, during a deployed configuration, to extend beyond the distal end of the trocar shaft 311. By providing the obturator as a translucent element it is possible to visualise anchor deployment by means of passing a camera through the lumen of the obturator. A distal end 1205 of the obturator 1200 is configured as a tissue dissector to assist in the presentation of the obturator through the abdominal wall during location of the device.

A head portion 1210 of the trocar is configured to receive an anchor pusher 1220. In this configuration the anchor pusher 1220 again comprises first and second needle drivers 240 that are provided on opposing sides of the trocar opening. Each of these are coupled to a common drive element 1230 that is moveable relative to the trocar head portion 1210 to allow a driving of the needle drivers down through first and second anchor channels 1235 in the head portion, through corresponding channels 1236 provided in the olive 1100 prior to contact with the needles that are disposed within the olive—as previously described.

FIG. 13 shows another arrangement in accordance with the present teaching which may be advantageously employed as part of a suture closure system. In this configuration a suture closure system comprises an olive 1300 providing a housing which is configured for operable receipt within an opening which is cut in an abdominal wall 1310. The olive housing 1300 defines an abdominal wall piercing 1315 or engaging portion and an outer resting portion 1320 which in use will rest against an outer surface 1311 of the abdominal wall 1310. The housing defines an aperture 1325 extending through to the abdominal wall engaging portion so as to define a lumen 1326 for allowing introduction of a trocar 1330 into the abdominal cavity.

As shown in the sectional view of FIG. 13C, the abdominal wall engaging portion 1315 is desirably dimensioned to extend through the skin 1312, the superficial fascia 1313 and into the deep fascial layer 1314 of the abdominal wall. It desirably is not sufficiently long to extend through the peritoneum 1316.

FIG. 14 shows the construct of the olive 1300 of FIG. 13 in more detail. In this exemplary arrangement it is formed in a multi-part construction comprising first 1401 and second 1402 parts that are co-operable with one another to encapsulate a third central part 1403. The third part comprises a shoulder element 1404 that is seatable within a channel 1405 provided in inner surfaces of each of the first and second parts. When each of the first and second parts are brought together, the channel becomes a continuous surface that extends circumferentially about the third part and by retaining the shoulder 1404 therein prevents vertical movement of the third part 1403 relative to the first and second parts.

When assembling the three parts to one another one or more screws or alternative securing means may be presented through apertures 1420 provided in each of the first and second parts. The retention of the first 1401 and second 1402 parts relative to one another causes an abutment of contact surfaces 1421 on each of the two parts against one another and locks the third part 1403 within a space defined between the two parts 1401, 1402.

Figure 14A:
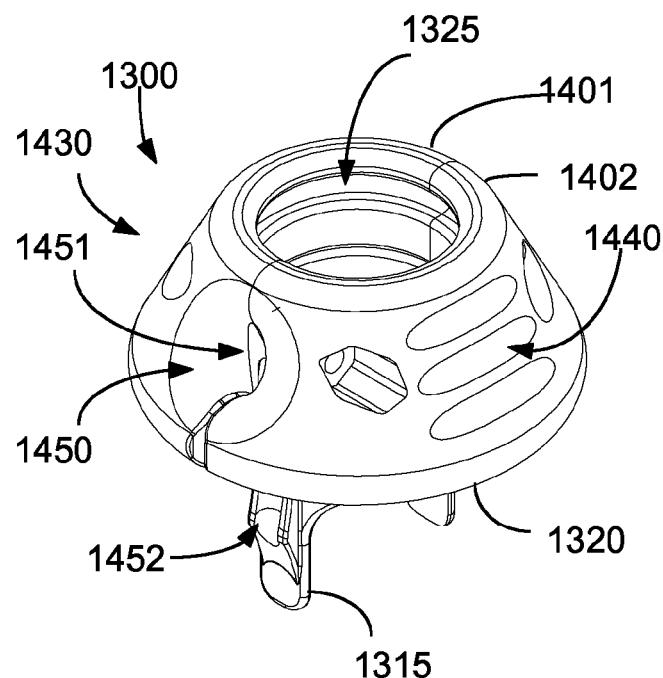
FIG. 14A shows an isometric view of the olive from FIG. 13.
Figure 14B:
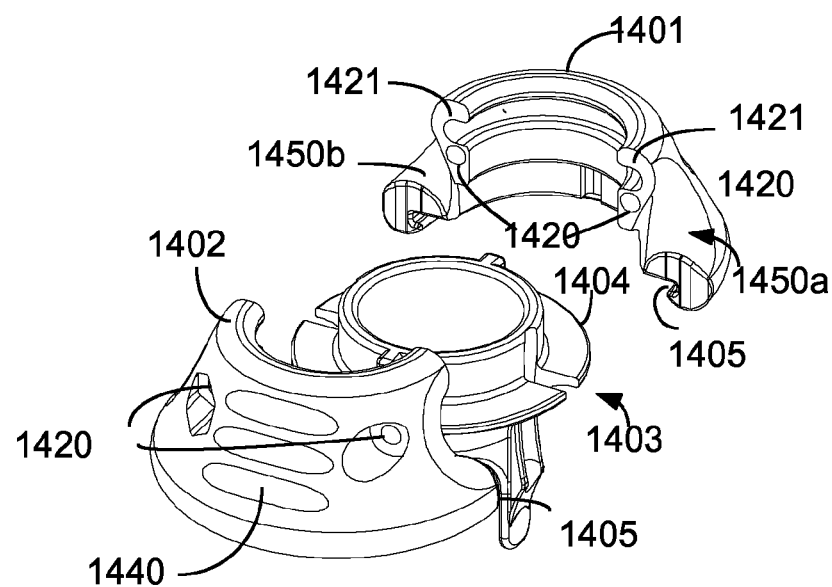
FIG. 14B shows an exploded view of the olive assembly.
Figure 14C:
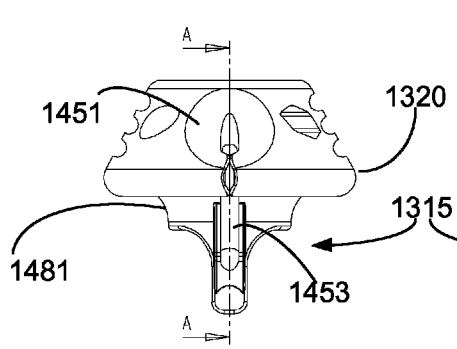
FIG. 14C shows the olive in end view.

As shown in FIG. 14A, once formed into an integral unit the olive 1300 defines an aperture 1325 provided in an upper portion 1430 of the olive 1300. The diameter of the aperture 1325 is sufficient to receive a trocar—as was shown in FIG. 13.

Edge surfaces 1440 of the olive may be textured or otherwise treated to provide finger grips to allow placement of a finger onto the olive and allow its correct positioning relative to the abdominal wall. This may allow the rotation of the olive relative to an aperture defined in the abdominal wall. Desirably two finger grips 1440 are provided on opposing sides of the aperture 1325.

The outer surface may also be dimensioned to receive first 1450a and second needle 1450b guide channels which are again provided on opposing sides of the aperture 1325. Each of the guide channels comprises an entry 1451 and an exit 1452 port. The entry port is desirably positioned above the abdominal wall engaging surface 1320 and exit port is provided within the abdominal wall engaging portion 1315. The needle channels allow presentation of a suture coupled to a needle through the olive on each of the two sides of the aperture 1325. It will be appreciated that the needle channels are distinct and separate from the lumen through which the trocar is placed such that needles can be provided through the needle channels independently of the occupancy of the lumen.

It will be appreciated from an inspection of FIG. 13B and FIG. 13C that the needle channels allow the presentation of a suture 1350 that is coupled to an anchor 1351 and driven using a needle driver 1352 through the abdominal wall where the anchor may then lodge against an inner surface 1317 of the abdominal wall. Tightening of the suture outwardly from the abdominal wall then retracts the anchor element 1351 against that surface so as to increase the tension in the suture. The suture may then be secured to anchor the olive relative to the abdominal wall as shown in FIG. 13C. By providing first and second sutures on the opposing sides of the aperture 1325 it is possible to anchor the olive at two sides thereby securing the anchor relative to the surgical site.

When the surgical procedure is complete, the sutures may be loosened and separated from the olive. This separation then allows the removal of the trocar and olive from the surgical site. As the sutures passed through the abdominal wall and are held within the wall by the anchors that will remain deployed within the abdominal cavity, a subsequent tightening of the sutures will cause the sides of the incision, or break in the abdominal cavity to be brought together to close the wound—as shown in FIG. 13D. The adoption of such a technique will advantageously require the use of bioabsorbable anchors 1351, as the anchors will remain within the abdominal cavity during the healing process prior to their ultimate disintegration.

Where it is desired not to leave such anchors within the abdominal cavity it is possible to dispense with anchors completely. FIGS. 13E through 13F show an alternative anchoring technique. In this configuration suture 1350 is passed into the abdominal cavity through one of the needle driver channels. A second channel is then used to allow the operator to introduce a needle 1360 having a eye 1361 disposed at a tip 1362 thereof, into the abdominal cavity. Using a separate tool, the surgeon will then be able to thread a free end of the suture 1350 through the eye. Retraction of the needle back through the needle driver channel will effect a removal of that suture from an opposite side of the opening to which it was introduced.—FIG. 13F. On subsequent completion of the surgical procedure, a tightening of the suture from one or both sides causes a closure of the wound to facilitate the healing process—FIG. 13G.

Figure 14D:
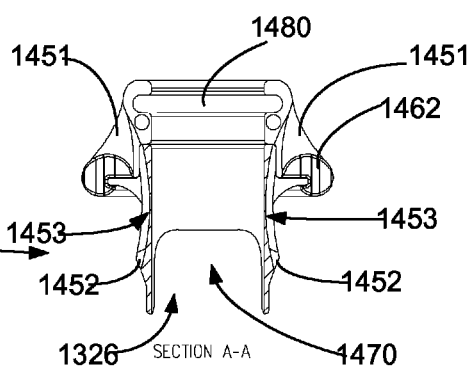
FIG. 14D is a section view of the olive.

As shown in FIG. 14D, the entry 1451 and exit ports 1452 of the needle channel are desirably separated by an arcuate path that presents a convex surface to the lumen 1326. This curved surface ensures that as the suture is driven through the olive it is then displaced away from a trocar such that the anchor site is spaced apart from the entry point of the trocar into the abdominal cavity. It will be understood that the angle of curvature of the needle channel affects the final delivery location of the suture relative to the entry point of the trocar into the abdominal cavity.

Figure 14E:
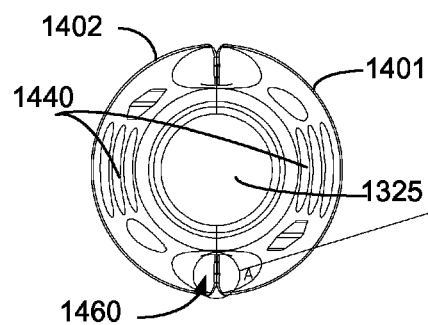
FIG. 14E shows the olive in plan view.
Figure 14F:
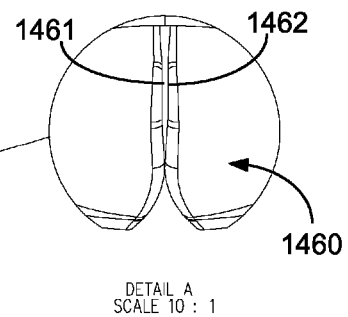
FIG. 14F is a detail view of a portion of FIG. 14E.

The olive may incorporate a suture securement feature adjacent or proximal to each of the entry ports 1451. This suture securement feature is useable to secure the suture once tightened against the olive, thereby self anchoring the olive relative to the abdominal wall. FIGS. 14E and 14F show detail of such a securement feature 1460 which comprises two opposing faces 1461, 1462 formed in each of the first and second parts 1401, 1402 but which when brought together form a double taper to which a suture may be presented and tightened within. In this way the suture securement feature operates as a jam cleat. These faces may be textured or otherwise treated to improve their suture retention properties.

As shown in FIG. 14, the abdominal wall engaging surface 1315 desirably comprises first and second cut-away portions provided in faces transverse to the exit ports 1452 of the needle engaging channels. These cut away portions 1470 define a tissue invagination zone within the abdominal wall engaging portion into which tissue may extend inwardly towards the lumen. It will be understood that this further assists in securing the olive relative to the abdominal wall and trocar as the ingress of the tissue within the tissue invagination zone restricts a rotation of the olive relative to the abdominal wall.

As shown in FIG. 14D the olive may also define an O-ring channel 1480 provided in an upper region of the olive and within the lumen. This O-ring channel provides a seat for an o-ring whose dimensions are selected to provide a compression fit against an inserted trocar. In this way once the trocar is provided through the lumen its outer surface will compress against the retained o-ring thereby sealing the lumen. Alternatively, a flat sheet of polymer could be used in place of the o-ring. This may be advantageously employed where the o-ring channel is placed on a mould split line.

The abdominal wall engaging portion also desirably comprises a sealing surface 1481 which provides a curved surface extending circumferentially about the olive and which in use is located against the skin layer 1312. This arcuate curved surface presents a concave surface to the skin against which it contacts, under a compressive force provided by the tightened sutures, thereby sealing against the skin.

The following describes an exemplary method of use whereby a device as described in FIG. 14 may be used as follows:

a) Make an initial incision in the abdominal wall
   b) Couple the olive device from FIG. 14 with a trocar
   c) Insert the trocar and olive into the incision
   d) Ensure the suture exit ports are positioned subcutaneously
   e) Insufflate the abdomen f) Take an anchor 1351 and load it onto the needle driver 1352 g) Drive the needle driver with attached anchor through the needle driver channel of the olive, then withdraw the needle driver, leaving the anchor and suture behind h) Repeat on the other needle driver channel.

i) Pull the suture strands taut and affix using the suture securement feature, which pulls the t-shaped anchor/suture against the inner abdominal wall.

j) Carry out the required surgery, at the end of which the sutures are pulled free of the suture securement feature, allowing the olive and trocar to be removed, k) Use the exposed suture strands to place a subcutaneous knot to close the wound An alternative method of using the device in an off midline location, where anchoring provided by the suture may not be required is described here:

a) Make an initial incision in the abdominal wall b) Couple the olive device from FIG. 14 with a trocar c) Insert the trocar and olive into the incision d) Ensure the suture exit ports are positioned subcutaneously e) Insufflate the abdomen f) Take an anchor 1351 and load it onto the needle driver 1352 g) Drive the needle driver with attached anchor through the needle driver channel of the olive, then withdraw the needle driver, leaving the anchor and suture behind h) Repeat on the other needle driver channel.

i) Carry out the required surgery, at the end of which the olive and trocar to be removed, j) Under direct visualisation the t-shaped anchors, which are hanging from the inner abdominal wall may then be picked up with a grasper, and pulled out of the trocar wound, ensuring that the exposed end of the suture does not get pulled into the abdominal wall, k) Repeat for the second anchor l) Once both anchors are removed externally, they may be joined and pulled back to the abdominal cavity by pulling on the exposed ends of the suture.

m) Use the exposed suture strands to place a subcutaneous knot to close the wound In a further embodiment the anchors may be made from a ferromagnetic material so that a magnet could be passed down the trocar and the anchors would be attracted to and adhere to the magnet, allowing them to be drawn out through the trocar. The advantage of this approach is that direct visualisation may not be necessary. However, the anchors would need to be removed prior to tying the suture in a loop. Alternatively the anchors may be themselves magnets and a ferromagnetic pick up device could be employed through the trocar to pick up the anchors. An exemplary method for using such a device may be:

(a) Make an initial incision in the abdominal wall (b) Couple an olive device such as that shown in FIG. 14 with a trocar (c) Insert the trocar and olive into the incision (d) Ensure the suture exit ports are positioned subcutaneously (e) Insufflate the abdomen (f) Take a magnetic anchor and load it onto the needle driver 1352

(g) Drive the needle driver with attached anchor through the needle driver channel of the olive, then withdraw the needle driver, leaving the anchor and suture behind (h) Repeat on the other needle driver channel.

(i) Complete the required surgery, at the end of which the sutures and anchors are left hanging from the abdominal wall.

(j) Remove the olive and trocar, (k) Insert a ferromagnetic grasper and pick up each of the magnetic anchors. Direct visualisation may be use to assist in this process.

(l) Remove the grasper bringing the magnetic anchors out through the wound, whilst ensuring that the opposite ends of the suture remain exposed.

(m) Use a scissors to remove the anchors and discard.

(n) Tie the two pieces of suture together, from which the anchors were removed (o) Pull on the opposite ends of the suture to draw the joined suture back into the wound (p) Use the exposed suture strands to place a subcutaneous knot to close the wound.

Figures 15A, 15B, 15C, 15D:
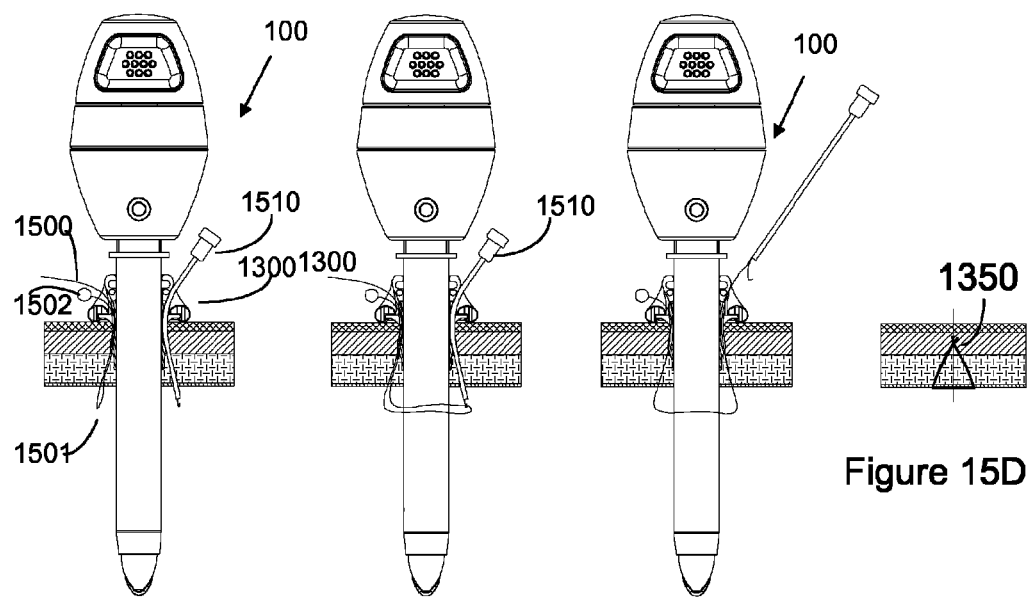
FIG. 15A to 15D shows the sequence of how a suture and olive in accordance with the present teaching may be used to close an abdominal defect with a suture loop.

FIGS. 15A through 15D provide an example of an alternative securing technique that may be utilised in accordance with the present teaching. This example is similar in form to that described with reference to FIGS. 13E through 13G in that suture is introduced at a first side of the wound in the abdominal wall and retrieved from a second side. In this configuration a suture 1500 is presented through the needle channel. In contrast to the arrangement of FIGS. 13C and 13D where the suture was coupled to an anchor that was driven into the abdominal cavity, in this arrangement the suture is provided in the form of a loop 1501 with an anchor 1502 provided at one end. In use, the loop 1501 is driven into the abdominal wall from one side of the lumen. A separate suture grabbing tool 1510 is provided through the needle channel on the opposing side of the lumen and into abdominal cavity. This suture grabbing tool is used to grab the loop 1501 and then pull the loop out through the needle channel. Once the suture grabbing tool is removed, the suture is pulled free creating a loop of suture through the fascia. On removal of the olive—post operatively—the tightening of the loop may be used to close the wound, as shown in FIG. 15D.

Figure 16A:
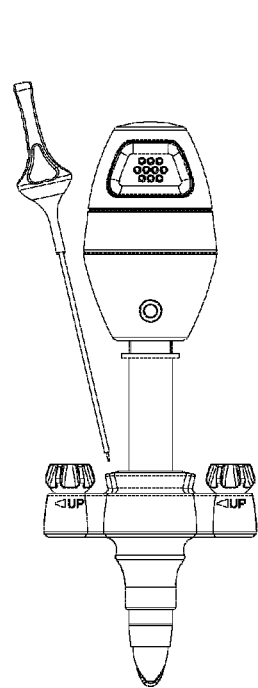
FIG. 16A shows a front elevation of a further example of an olive in use with a trocar.
Figure 16B:
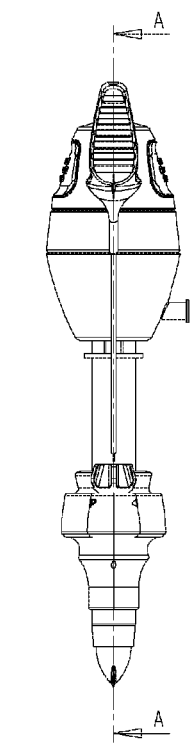
FIG. 16B is an end view of the same device.
Figure 16C:
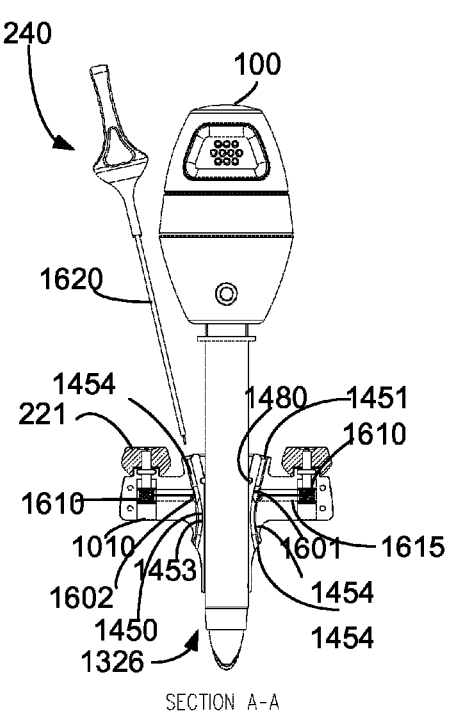
FIG. 16C is a sectioned view of the device of 16A.

FIG. 16 shows a configuration which shares components previously described with reference to FIG. 9—the integrated suture spool with roller clutch and winder—and the arcuate needle channel of FIGS. 14 and 15. In this configuration the suture is provided integrally within the olive on a rolled spool 1610. An anchor 1601 is coupled to the suture and disposed within the needle channel 1450. The anchor is provided with a suture guide pin 1602 located on the spool side of the anchor. The guide pin 1602 is dimensioned to be located within a channel 1615 extending from the spool 1610 in a direction substantially transverse to the lumen 1326. This allows the location of the anchor against the end portion of this channel on retraction of the suture onto its spool. An additional channel 1454 is provided which runs parallel to the needle channel 1450. This channel is sized for the suture and in use allows the suture to run freely when the needle channel 1450 is occupied with the needle driver 1620. This feature also inhibits rotation of the needle relative to the needle driver which enables more accurate needle deployment. In a further embodiment, rotation of the anchor about the needle driver could be prevented by making the profile of the anchor oval and engaging it with a flat on the needle driver. It will be appreciated that various shapes may be employed to achieve a non rotate feature, and that the example given is not limiting. Such a non rotate feature may be usefully employed in an application where it is required to orientate the angled cut of a needle in a given orientation.

In this configuration the anchor is orientated within the channel such that it will exit outwardly away from the end portion of the trocar.

In use, when the needle driver 1620 is presented into the needle entry port 1451 (which in this configuration is provided on an upper surface of the olive) it moves within the channel until such time as it meets with the anchor 1601 that is located within the channel. It then drives the anchor through the channel until it exits through the exit port 1452 where it extends into the abdominal cavity. At this time the needle driver can then be withdrawn and the suture spool tightened to effect a retraction of the anchor towards the olive.

To allow the needle driver to pass through the arcuate needle channel 1450 it is desirably at least partially flexible.

Figures 17A, 17B, 17C, 17D:
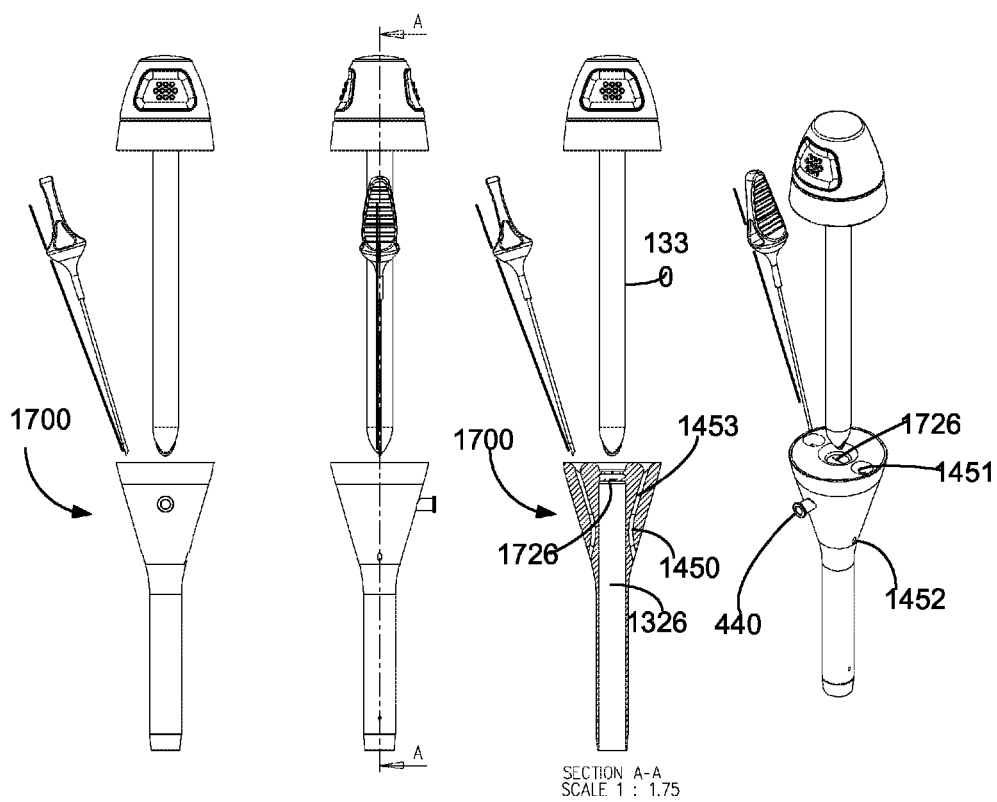
FIG. 17A shows a further example of a combined trocar/olive device.
FIG. 17B shows the device of FIG. 17A in end view.
FIG. 17C shows the device of FIG. 17A in sectioned view.
FIG. 17D shows an isometric view of the device.

FIG. 17 shows a further alternative wherein the olive is integrated into the trocar provided with a lumen 1326 through which a presented obturator 1330 may pass. The lumen is provided with a slit seal 1726 at an upper region of which—the slit seal securing against the outer surface of the obturator 1330 once it is presented within the lumen. Similarly to that already described first and second needle guide channels are provided on opposite sides of the lumen. The guide channels present an arcuate convex inner surface proximal to the lumen such that when a needle driver is driving an anchor through the channel it will exit outwardly and away from the lumen 1326. The entry ports 1451 for the needle channel are provided in a similar method to FIG. 16.

Figures 18A, 18B, 18C, 18D:
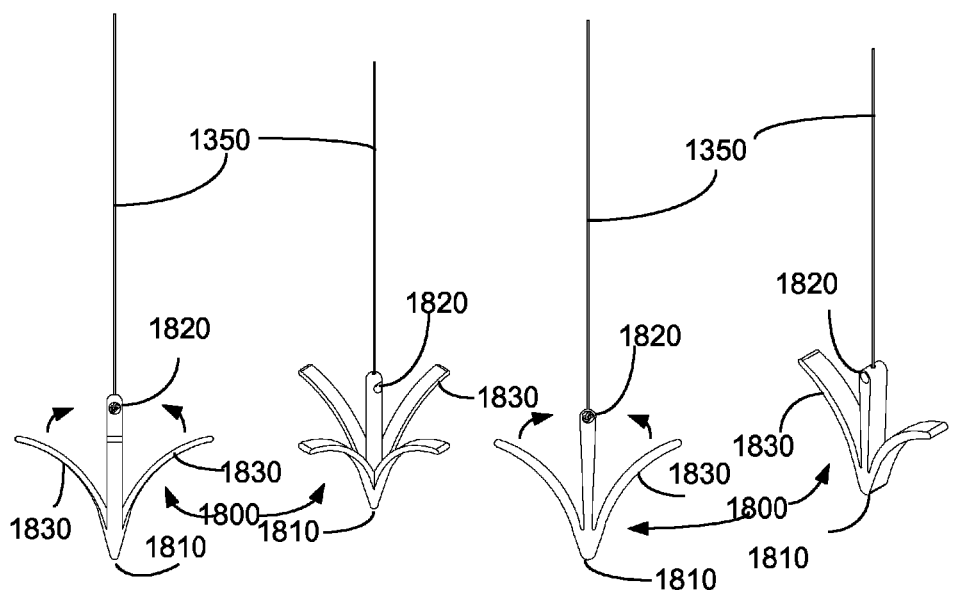
FIGS. 18A to 18D show examples of anchors that may be provided in accordance with the present teaching.

FIG. 18 shows example of anchors 1800 that may be employed within the present teaching. In each of the exemplary arrangements the anchors comprise a head portion 1810 and a suture coupling portion 1820 at opposing ends of the anchor. Two or more barbs 1830 are also provided. The barbs are at least partially flexible and are orientated that in the absence of an applied force thereon will extend outwardly from the head 1810. When being driven through the needle channel, the barbs 1830 are displaced inwardly to be substantially parallel with the major longitudinal axis of the anchor—that axis extending from the head 1810 to the suture coupling portion 1820. In this way the cross sectional area of the anchor is reduced when it is passing through the needle guide channel but once exiting from the channel the barbs will extend outwardly. On tensioning the suture the barbs will then serve to anchor against the abdominal wall and secure the olive to the abdominal wall. While the head portion 1810 is illustrated here with a radiused tip, this is not intended to be limiting, as the head portion may feature any number of needle tip configurations.

Figures 19A, 19B, 19C:
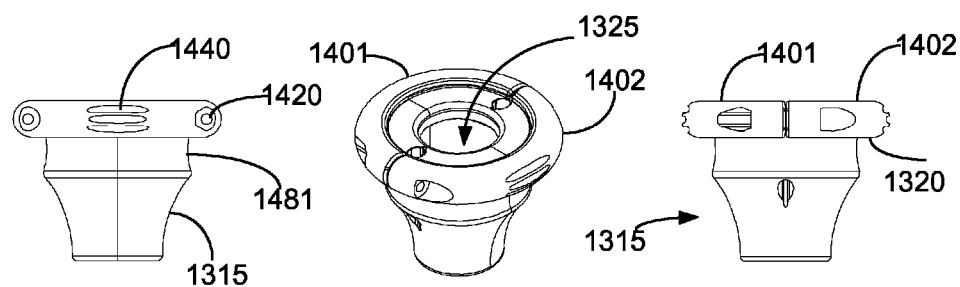
FIG. 19A shows a further example of an olive in elevation view, while the same olive appears in side view in FIG. 19C, and isometric view in FIG. 19B.

In a further embodiment the olive from FIG. 14, FIG. 19 or FIG. 20 could be used in conjunction with the device in FIG. 13E method for using such a device may be as described follows:

(a) Make an initial incision in the abdominal wall
(b) Couple the olive device from FIG. 14, FIG. 19 or FIG. 20 with a trocar
(c) Insert the trocar and olive into the incision
(d) Ensure the suture exit ports are positioned subcutaneously
(e) Insufflate the abdomen
(f) Take the needle driver from FIG. 13E which has a preloaded suture and drive it through the needle driver channel of the olive, and then withdraw the needle driver, leaving the anchor and suture behind
(g) Drive the needle driver through the opposite needle driver channel of the olive
(h) Under direct visualisation, use a grasper or suture picker to thread the suture back through the eyelet of the needle driver.
(i) Remove the needle driver, which will draw the suture out with it, leaving a complete loop of suture running from one side of the olive, through the needle guide channel into the peritoneum, through the opposite needle guide channel and out on the opposite side of the olive
(j) Use the suture securement features to secure the suture and anchor the olive, if desired.
(k) Carry out the required surgery, at the end of which the sutures are in place through the fascia.
(l) Remove the olive and trocar after disengaging the suture from the suture securement feature,
(m) Use the exposed suture strands to place a subcutaneous knot to close the wound.

FIGS. 19 and 20 show examples of olives in accordance with the present teaching. It will be recalled from the discussion of FIG. 14 that an olive in accordance with the present teaching may be provided in a multi-part construction. Such an assembly is also common to the arrangements of these Figures where the same reference numerals will be used for similar parts. First 1401 and second 1402 parts of the olive are co-operable with one another to define an aperture 1325 through which a trocar may operably pass.

The olive comprises an abdominal wall engaging portion 1315 and an outer resting portion 1320 which in use will rest against an outer surface of the abdominal wall. Similarly to the arrangement of FIG. 14, in this example the abdominal wall engaging portion 1315 is desirably dimensioned to extend through the skin, the superficial fascia and into the deep fascial layer of the abdominal wall. It desirably is not sufficiently long to extend through the peritoneum. In the configuration of FIG. 19 the abdominal wall engaging portion is continuous about its circumference such that, in location, the abdominal wall will contact the surface continuously.

Grip portions 1440 are provided on an outer surface of the olive. The two parts 1401, 1402 are secured relative to one another desirably using a screw or other fastener.

Figures 20A, 20B, 20C:
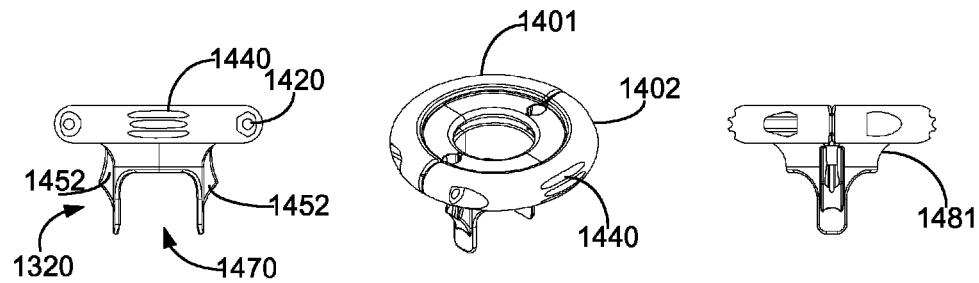
FIG. 20A shows a further example of an olive in elevation, while the same olive appears in side view in FIG. 20C, and isometric view in FIG. 20B.

FIG. 20A through 20C show an arrangement similar to that shown in FIG. 14 where the abdominal wall engaging surface 1320 desirably comprises first and second cut-away portions 1470 provided in faces transverse to the exit ports 1452 of the needle engaging channels. These cut away portions 1470 define a tissue invagination zone within the abdominal wall engaging portion into which tissue may extend inwardly towards the lumen. It will be understood that this further assists in securing the olive relative to the abdominal wall and trocar as the ingress of the tissue within the tissue invagination zone restricts a rotation of the olive relative to the abdominal wall.

The suture/anchor assembly may consist of a length of bio-absorbable suture attached to a length of bio-absorbable tubing in one embodiment such that the assembly is t-shaped. The suture may be a braided suture made from a bioabsorbable polymer such as PGA for example. For fascial layer closure a USP size 0 suture is preferred. This material is ideally suited to an application where the suture maintains approximately 50% of its strength after two weeks. However it will be appreciated that the suture material may be changed depending strength or mass loss requirements of the specific application.

A braided suture has the advantage of securely holding a knot, which is well suited to the construction method illustrated in FIGS. 13C, 21A and 21B. Here a short length of PGLA tubing has a hole made in its side wall. The suture is threaded through this hole and knotted with a double overhand knot. The knot is then pulled back into the main lumen of the tubing, the knot being too large to come through the hole on the side wall. It will be appreciated that while a double overhand knot is used in this embodiment the disclosure of such is not intended to limit the type of knot used. Additionally braided suture is not as prone to taking a shape set when wound tightly on a spool as monofilament is, making braided suture a preferred option on devices disclosed above which entail the suture being wound on a spool.

In an application where anchors are not delivered through the abdominal wall, for example FIG. 13E or FIG. 15, a monofilament suture could be used. Polydioxanone (PDS) and Poly(glycolide-co-caprolactone) (Poliglecaprone 25) are examples of such materials. A disadvantage of monofilament suture is its reduced knot strength when compared to a comparably sized braided suture. An assembly employing monofilament suture may include a larger diameter suture, or be crimped into the needle if the needle is a stainless steel option. Where the suture is attached to a bio-absorbable anchor there is the option of heat welding the two components together or passing the suture through a narrow hole in the anchor and heat forming the tip of the suture, so that it does not pass back through the hole. Another option would be to place multiple barbs on the suture so that the suture itself acts as an anchor.

The anchor in this configuration consists of an extruded tube. The hole in the side wall is sized to suit the suture diameter and may be disposed at the centre of the extruded length. The tubing material in an exemplary arrangement is Poly(L-lactide-co-glycolide) (PLGA) but could be made from any ratios of the following materials Poly(L-lactide-co-glycolide) (PLGA), Polylactic acid (PLA), Polyglycolide (PGA), Polydioxanone (PDS), Polycaprolcatone (PCL). In one example of use, the sutures and needle anchors may be composed of a fast degrading polymer. In another embodiment the sutures and needle anchors may be composed of a slow degrading polymer. In another variant the needle anchors may have an additional coating of Polylactic acid (PLA) or Polycaprolactone (PCL) or a co-polymer blend of these polymers in order to vary the degradation profile. In another case, the degree of crystallisation of the polymer composition of the needle anchors may be altered through heating and cooling treatments to change its mechanical properties.

FIG. 21 shows various examples of anchors that may be deployed in accordance with the present teaching. In the arrangement of FIG. 21A a suture 2101 is passed through an aperture 2102 in the body of the anchor 2103. As shown in the section view of FIG. 21B, a knot 2104 may then be tied to retain the suture relative to the anchor. The anchor body 2103 is desirably hollow to allow both for location of the knot within the body, but also to allow for engagement of a needle driver with the anchor to enable its presentation through the abdominal wall into the abdominal cavity. An end surface 2105 is chamfered or otherwise sharpened to provide a driving surface to facilitate the passage through the abdominal wall. The opposing end 2106 is desirably the end that engages with the needle driver, not shown.

FIG. 21C shows an alternative coupling arrangement for facilitating tethering of the anchor to suture. In this configuration the suture passes through the body 2107 of the anchor—first and second apertures are provided to facilitate this passage. On threading the suture through the body it may then be tied against itself to retain the anchor within a loop. First and second anchors could be retained against one another by passing a first anchor through the loop formed for the second.

Figure 21D:
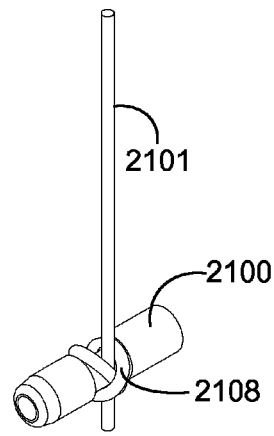
Figure 21E:
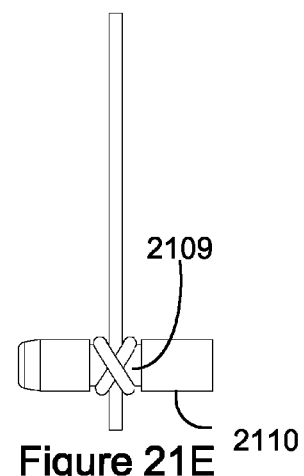

FIGS. 21D and 21E shows a further arrangement whereby suture 2101 is tied around an outer surface of an anchor 2100 in an knot 2108. In this arrangement the knot is located within a recessed portion 2109 of the outer body of the anchor. In this way the physical formation of the knot does not project substantially beyond the major surface 2110 of the anchor.

Figure 21F:
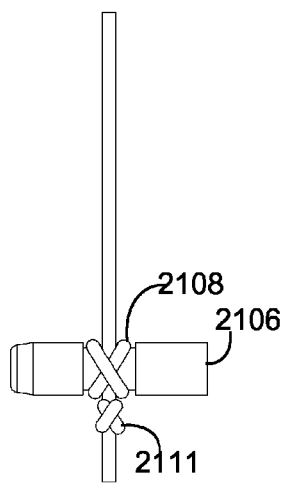
Figure 21G:
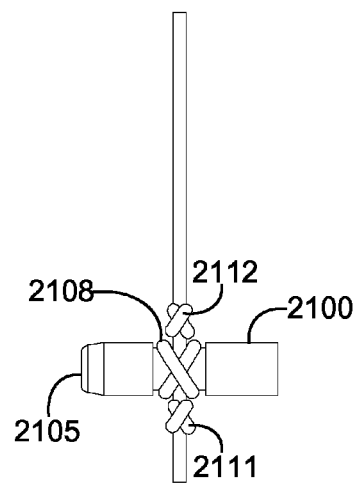
Figure 21H:
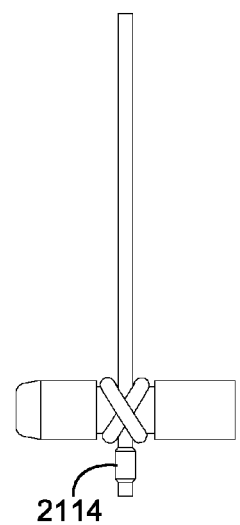
Figures 22A, 22B:
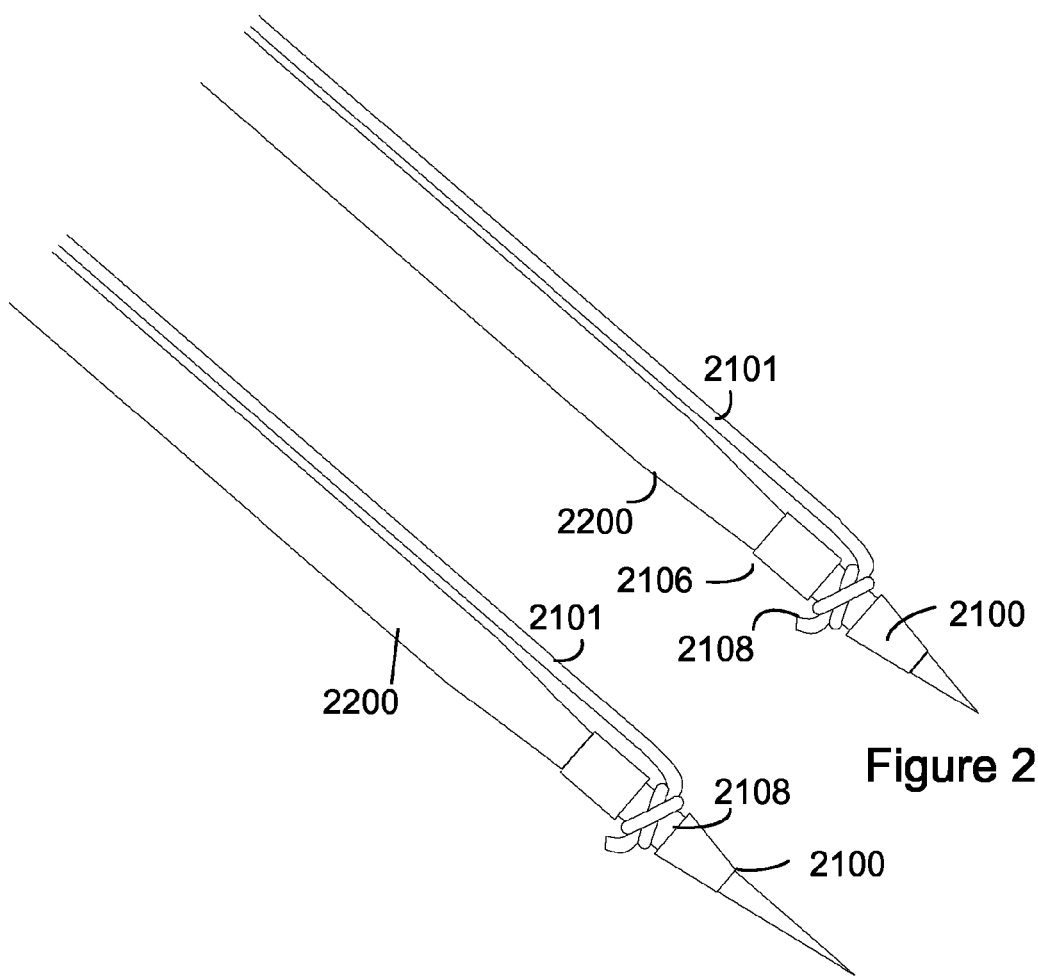
FIGS. 22A and 22B show examples of how suture may be delivered within the abdominal cavity in accordance with the present teaching.

As shown in FIG. 21F, the location of the knot 2108 to the anchor may be more closely secured by provision of a second knot 2111 below the anchor. Further securing could be facilitated by a third knot 2112 above the anchor such as shown in FIG. 21G. Another alternative is a heat formed flat 2114 provided such as the example of FIG. 21H FIG. 22 shows how a needle driver 2200 may engage with an anchor 2100—such as the examples of FIG. 21 and then drive the anchor forwardly. As is shown, the needle driver 2200 engages with an end surface of the anchor. Pushing the needle forwardly through an olive—such as that described above—effects a corresponding movement of the anchor through and into the abdominal cavity While preferred arrangements have been described in an effort to assist in an understanding of the teaching of the present invention it will be appreciated that it is not intended to limit the present teaching to that described and modifications can be made without departing from the scope of the invention.

It will be appreciated that the exemplary arrangements or examples of devices have been described with reference to the Figures attached hereto. Where a feature or element is described with reference to one Figure, it will be understood that the feature or element could be used with or interchanged for features or elements described with reference to another Figure or example. The person of skill in the art, when reviewing the present teaching, will understand that it is not intended to limit the present teaching to the specifics of the illustrated exemplary arrangements as modifications can be made without departing from the scope of the present teaching.

The words comprises/comprising when used in this specification are to specify the presence of stated features, integers, steps or components but does not preclude the presence or addition of one or more other features, integers, steps, components or groups thereof.

The invention claimed is:

1. A suture closure system configured for engagement with an aperture provided in an abdominal wall, the system comprising:
   a housing defining a lumen for receipt of a trocar, the housing comprising an abdominal wall engaging portion and an outer resting portion which in use will rest against an outer surface of the abdominal wall, the abdominal wall engaging portion extending circumferentially about and being separate to the lumen;
   the housing further comprising a first needle guide channel provided in a side wall of the abdominal wall engaging portion and a second needle guide channel provided in a side wall of the abdominal wall engaging portion, each of the first needle guide channel and the second needle guide channel enclosed within the side wall of the abdominal wall engaging portion, each of the first needle guide channel and the second needle guide channel being provided on opposite sides of the lumen respectively and having a diameter smaller than a diameter of the lumen, each of the needle guide channels having an entry port for receiving a needle driver, the entry port being positioned above the abdominal wall engaging portion, and an exit port being located above a distal end portion of the abdominal wall engaging portion, the exit port providing an exit from the needle guide channel through which a suture may exit the housing and into the abdominal wall, the entry and exit ports for each needle guide channel being provided on the same side of the lumen, the guide channels providing a convex surface proximal to the lumen such that the suture will exit the side wall of the abdominal wall engaging portion away from the lumen and into the abdominal wall on being displaced out of the needle guide channel.

2. The system of claim 1 wherein the lumen is dimensioned for receiving a trocar.

3. The system of claim 1 wherein the housing is provided in a multi-part construction comprising first and second parts that are co-operable with one another to encapsulate a third central part.

4. The system of claim 3 wherein the third part comprises a shoulder element that is seatable within a channel provided in inner surfaces of each of the first and second parts.

5. The system of claim 4 wherein on bringing the first and second parts together the channel defines a continuous surface that extends circumferentially about the third part retaining the shoulder therein and restricting vertical movement of the third part relative to the first and second parts.

6. The system of claim 1 comprising a suture securement feature for securing a suture relative to the housing.

7. The system of claim 6 wherein the housing is provided in a multi-part construction comprising first and second parts that are co-operable with one another to encapsulate a third central part and wherein the suture securement feature comprises two opposing faces formed in each of the first and second parts which when brought together form a cleat.

8. The system of claim 1 wherein the abdominal wall engaging surface comprises first and second cut-away portions provided in faces transverse to the exit ports of the needle guide channels, the cut away portions defining a tissue invagination zone within the abdominal wall engaging portion into which tissue may extend inwardly towards the lumen.

9. The system of claim 1 configured for engagement with an aperture provided in the abdominal wall, the housing comprising an abdominal wall piercing or engaging portion and an outer resting portion which in use will rest against an outer surface of the abdominal wall and wherein the abdominal wall engaging portion comprises a sealing surface which provides a curved surface extending circumferentially about the housing and which in use is located against the abdominal wall.

10. The system of claim 9 wherein the sealing surface is an arcuate curved surface which operably presents a concave surface to the skin against which it contacts, under a compressive force provided by tightened sutures, thereby sealing against the skin.

11. The system of claim 1 wherein the housing defines an O-ring channel within the lumen, the O-ring channel providing a seat for an O-ring whose dimensions are selected to provide a compression fit against inserted surgical instrumentation such that on providing the surgical instrumentation through the lumen its outer surface will compress against a retained O-ring thereby sealing the lumen.

12. The system of claim 1 wherein the needle guide channels are tapered such that a needle will exit at a fixed angle between 5 and 30°.

13. The system of claim 1 comprising a needle driver by which an operator may operably apply a downward pressure onto a needle.

14. The system of claim 1 wherein the exit port is located such that operably a needle will pass into a subcutaneous layer of the abdominal wall on exiting the needle guide channel.

15. The system of claim 1 comprising a trocar, the trocar being receivable into an abdominal cavity through the lumen.

16. A laparoscopic surgical method comprising:
 a. making an incision and providing a system as claimed in claim 1;
 b. providing the surgical instrument through the lumen of the housing;
 c. inserting the combined surgical instrument and housing assembly into the incision;
 d. insufflating the abdomen;
 e. using a needle driver to drive suture needles inside the abdominal cavity, and then withdrawing the needle drivers;
 f. anchoring the housing by tautening the sutures, and drawing the needles flush against the peritoneum, at which point the suture is locked;
 g. completing the required surgery, at the end of which the housing is removed by unlocking the suture; and
 h. tying one or multiple knots in the suture pushing the knot subcutaneously.

* * * * *